US011590154B2

(12) United States Patent
Fathi et al.

(10) Patent No.: US 11,590,154 B2
(45) Date of Patent: Feb. 28, 2023

(54) TRIPLE ANTIBIOTIC FIXED-DOSE COMBINATION PRODUCTS, DOSING REGIMEN, METHODS, AND KITS FOR TREATING PULMONARY NON-TUBERCULOSIS MYCOBACTERIAL INFECTIONS

(71) Applicant: RedHill Biopharma Ltd., Tel-Aviv (IL)

(72) Inventors: Reza Fathi, Oradell, NJ (US); Gilead Raday, Tel-Aviv (IL); Patricia Anderson, Brampton (CA); Elliot Offman, Richmond Hill (CA)

(73) Assignee: RedHill Biopharma Ltd., Tel-Aviv (IL)

( * ) Notice: Subject to any disclaimer, the term of this patent is extended or adjusted under 35 U.S.C. 154(b) by 146 days.

(21) Appl. No.: 17/364,124

(22) Filed: Jun. 30, 2021

(65) Prior Publication Data

US 2021/0401865 A1  Dec. 30, 2021

Related U.S. Application Data

(60) Provisional application No. 63/046,335, filed on Jun. 30, 2020, provisional application No. 63/046,322, filed on Jun. 30, 2020.

(51) Int. Cl.
| | |
|---|---|
| *A61K 31/7048* | (2006.01) |
| *A61K 31/438* | (2006.01) |
| *A61P 31/04* | (2006.01) |
| *A61K 9/00* | (2006.01) |
| *A61K 47/10* | (2017.01) |
| *A61K 31/498* | (2006.01) |

(52) U.S. Cl.
CPC ........ *A61K 31/7048* (2013.01); *A61K 9/0053* (2013.01); *A61K 31/438* (2013.01); *A61K 31/498* (2013.01); *A61K 47/10* (2013.01); *A61P 31/04* (2018.01)

(58) Field of Classification Search
None
See application file for complete search history.

(56) References Cited

U.S. PATENT DOCUMENTS

| | | |
|---|---|---|
| 6,277,836 B1 | 8/2001 | Borody |
| 8,343,511 B2 | 1/2013 | Borody et al. |
| 10,434,114 B2 | 10/2019 | Borody et al. |
| 2018/0273573 A1 | 9/2018 | Tan et al. |

FOREIGN PATENT DOCUMENTS

WO    2017/194734 A1    11/2017

OTHER PUBLICATIONS

Agins et al., "Effect of Combined Therapy with Ansamycin, Clofazimine, Ethambutol, and Isoniazid for *Mycobacterium avium* Infection in Patients with AIDS", The Journal of Infectious Diseases, vol. 159, No. 4, Apr. 1989.

Van Ingen et al., "Resistance mechanisms and drug susceptibility testing of nontuberculous mycobacteria", Drug Resistance Updates 15 (2012) 149-161.
Cholo et al., "Clofazimine: current status and future prospects", Journal of Antimicrobial Chemotherapy 2012; 67:290-298.
Fernandes et al., "In Vitro and In Vivo Activities of Clarithromycin against *Mycobacterium avium*", Antimicrobial Agents and Chemotherapy, Sep. 1989, pp. 1531-1534, vol. 33, No. 9.
Ferro et al., "Clofazimine Prevents the Regrowth of *Mycobacterium abscessus* and *Mycobacterium avium* Type Strains Exposed to Amikacin and Clarithromycin", Antimicrobial Agents and Chemotherapy, Feb. 2016, vol. 60, No. 2, pp. 1097-1105.
Field et al., "*Mycobacterium avium* complex Pulmonary Disease in Patients Without HIV Infection", Chest Journal, 126, Aug. 2, 2004, pp. 566-581.
Griffith et al., "Early Results (at 6 Months) with Intermittent Clarithromycin-Including Regimens for Lung Disease Due to *Mycobacterium avium* Complex", Clinical Infectious Diseases, Feb. 2000, 30, pp. 288-292.
Griffith et al., "Clinical and Molecular Analysis of Macrolide Resistance in *Mycobacterium avium* Complex Lung Disease", Am J Respir Crit Care Med, vol. 174, pp. 928-934, 2006.
Griffith et al., "An Official ATS/IDSA Statement: Diagnosis, Treatment, and Prevention of Nontuberculous Mycobacterial Diseases", Am J Respir Crit Care Med, vol. 175, pp. 367-416, 2007.
Horgen et al., "Postantibiotic effect of amikacin, rifampin, sparfloxacin, clofazimine and clarithromycin against *Mycobacterium avium*", Res. Microbiol., 1997, 148, pp. 673-681.
Jansons et al., "Clofazimine and Liposomes Enhance the Susceptibility of Intracellular *Mycobacterium avium* toward Rifabutin", Current Microbiology vol. 20 (1990), pp. 261-264.
Jarand et al., "Long-term Follow-up of *Mycobacterium avium* Complex Lung Disease in Patients Treated With Regimens Including Clofazimine and/or Rifampin", Chest 2016; 149(5), pp. 1285-1293.
Jarzembowski et al., "Nontuberculous Mycobacterial Infections", Arch Pathol Lab Med—vol. 132, Aug. 2008, pp. 1333-1341.
Jeong et al., "Intermittent Antibiotic Therapy for Nodular Bronchiectatic *Mycobacterium avium* Complex Lung Disease", American Journal of Respiratory and Critical Care Medicine, vol. 191, No. 1, Jan. 2015, pp. 96-103.
Klemens et al., "Activity of Clarithromycin against *Mycobacerium avium* Complex Infection in Beige Mice", Antimicrobial Agents and Chemotherapy, vol. 36, No. 11, Nov. 1992, pp. 2413-2417.

(Continued)

*Primary Examiner* — Dale R Miller
(74) *Attorney, Agent, or Firm* — Greenberg Traurig, LLP

(57) ABSTRACT

A fixed-dose combination drug product formulated for oral delivery comprises a fixed 158.3 mg dose of clarithromycin, a fixed 13.3 mg dose of clofazimine and a fixed 40.0 mg dose of rifabutin. The fixed-dose combination drug product is sufficiently designed for use in treating pulmonary *Mycobacterium avium* Complex (MAC) disease in a subject in need thereof. A method for treating MAC disease in a human having MAC lung infection comprising orally administering, twice daily, about 475 mg of clarithromycin, about 40 mg of clofazimine and about 120 mg of rifabutin. A kit for treating pulmonary MAC disease in an individual having MAC lung infection comprises a supply of fixed-dose combination drug products, wherein each of the fixed-dose combination drug products comprise a fixed 158.3 mg dose of clarithromycin, a fixed 13.3 mg dose of clofazimine and a fixed 40.0 mg dose of rifabutin; and instructions for use.

20 Claims, 10 Drawing Sheets

(56) References Cited

OTHER PUBLICATIONS

Li et al., "Antimicribial susceptibility and MIC distribution of 41 drugs against clinical isolates from China and reference strains of nontuberculous mycobacteria", International Journal of Antimicrobial Agents, 49 (2017), pp. 364-374.

Martiniano et al., "Safety and Effectiveness of Clofazimine for Preliminary and Refractory Nontuberculous Mycobacterial Infection", Chest, (2017), doi: 10.1016/j.chest,2017.04.175.

Morimoto et al., "Macrolide-Resistant *Mycobecterium avium* Complex Lung Disease: Analysis of 102 Consecutive Cases", AnnalsATS, vol. 13 No.11, Nov. 2016. pp. 1904-1911.

Naik et al., "In Vitro Activities of Several New Macrolide Antibiotics against *Mycobacterium avium* Complex", Antimicrobial agents and Chemotherapy, Sep. 1989, vol. 33 No.9, pp. 1614-1616.

O'Brien et al., "Rifabutin (Ansamycin LM 427): A New Rifamycin-S Derivative for the Treatment of Mycobacterial Diseases", Reviews of Infectious Diseases. vol. 9, No. 3 (May-Jun. 1987), pp. 519-530.

Orme, "Antimycobacterial Activity In Vivo of LM427 (Rifabutin)", Am Rev Respir Dis 1986; 138; pp. 1254-1257.

Gangadharam et al., "Activity of Rifabutin Alone or in Combination with Clofazimine or Ethambutol or Both Against Acute and Chronic Experimental *Mycobacterium* intracellulare Infections", Am Rev Respir Dis 1987; 136, pp. 329-333.

Perronne et al., "Activities of Clarithromycin, Sulfisoxazole, and Rifabutin against *Mycobacterium avium* Complex Multiplication within Human Macrophages", Antimicrobial Agents and Chemotherapy. Aug. 1990, vol. 34, No. 8, pp. 1508-1511.

Perronne et al., "Activities of Sparfloxacin, Azithromycin, Temafloxacin, and Rifapentine Compared with That of Clarithromycin against Multiplication of *Mycobacterium avium* Complex within Human Macrophages", Antimicrobial Agents and Chemotherapy. Jul. 1991, vol. 35, No. 7, pp. 1356-1359.

Pinheiro et al., "Differential Interactions of Rifabutin with Human and Bacterial Membranes: Implication for Its Therapeutic and Toxic Effects", Journal of Medicinal Chemistry, 2013, 56, pp. 417-426.

Rastogi et al., "French Multicenter Study Involving Eight Test Sites for Radiometric Determination of Activities of 10 Antimicrobial Agents against *Mycobacterium avium* Complex", Antimicrobial Agents and Chemotherapy, Mar. 1995, vol. 39, No. 3, pp. 638-644.

Rastogi et al., "Extracellular and Intracellular Activities of Clarithromycin Used Alone and in Association with Ethambutol and Rifampin against *Mycobacterium avium* Complex", Antimicrobial Agents and Chemotherapy, Mar. 1991, vol. 35, No. 3, pp. 462-470.

Saito et al., "Activity of Rifabutin Alone and in Combination with Clofazimine, Kanamycin and Ethambutol Against *Mycobacterium* Intracellulare Infections in Mice"; Tubercle (1989) 70, p. 201-205.

Shen et al., "High efficacy of clofazimine and its synergistic effect with amikacin against rapidly growing mycobacteria", International Journal of Antimicrobial Agents, 35 (2010) pp. 400-404.

Skinner et al., "Pharmacokinetics of Rifabutin", Antimicrobial Agents and Chemotherapy, Aug. 1989, vol. 33, No. 8, pp. 1237-1241.

Swanson et al., "Pharmacokinetics and Pharmacodynamics of Clofazimine in a Mouse Model of Tuberculosis", Antimicrobial Agents and Chemotherapy, Jun. 2015, vol. 59, No. 6, pp. 3042-3051.

Van Ingen et al., "The Pharmacokinetics and Pharmacodynamics of Pulmonary *Mycobacterium avium* Complex Disease Treatment", American Journal of Respiratory and Critical Care Medicine, vol. 186, 2012, pp. 559-565.

Wallace Jr., et al., "Macrolide/Azalide Therapy for Nodular/Bronchiectatic *Mycobacterium avium* Complex Lung Disease", Chest, 146 # Aug. 2, 2014, pp. 276-282.

Yajko et al., "In Vitro Activities of Rifabutin, Azithromycin, Ciprofloxacin, Clarithromycin, Clofazimine, Ethambutol, and Amikacin in Combinations of Two, Three, and Four Drugs against *Mycobacterium avium*", Antimicrobial Agents and Chemotherapy, Mar. 1996, vol. 40, No. 3, pp. 743-749.

International Search Report and Written Opinion from International Application No. PCT/IB2021/000451 dated Feb. 2, 2022.

US 11,590,154 B2

TRIPLE ANTIBIOTIC FIXED-DOSE COMBINATION PRODUCTS, DOSING REGIMEN, METHODS, AND KITS FOR TREATING PULMONARY NON-TUBERCULOSIS MYCOBACTERIAL INFECTIONS

RELATED APPLICATIONS

This application claims the benefit of and priority to U.S. Provisional Patent Application No. 63/046,322, filed Jun. 30, 2020 and U.S. Provisional Patent Application No. 63/046,335, filed Jun. 30, 2020, the entirety of these applications are hereby incorporated herein by reference.

BACKGROUND

Organisms of the *Mycobacterium* genus are widely distributed in the environment and can be found forming biofilms in water pipes and potable water tanks. Some Mycobacteria species are highly virulent and may spread from host to host by coughing and inhalation or direct contact, causing leprosy (*M. leprae*) or tuberculosis (*M. tuberculosis*). Other Mycobacteria species are significantly less virulent and are collectively referred to as Non-Tuberculous Mycobacteria (NTM). Although NTM are less virulent, under certain circumstances they may infect hosts with weakened immune systems or a particular physiology (such as bronchiectasis). Such infection of the host may occur by two different routes. One is the gastro-intestinal route, from where the bacteria can disseminate or/and cause lymph node infection. The other is the respiratory route, by which the bacterium causes infection in individuals with chronic pulmonary conditions (bronchiectasis, emphysema, cystic fibrosis, chronic obstructive pulmonary disease). The latter route of infection is common in individuals with underlying lung disease, and the lung infection is associated with the formation of biofilm (Carter G, et al, AAC 48:4907, 2004; Yamazaki Y, et al Cell Microbiol, 8: 808. 2006). NTM is on the Food and Drug Administration's list of "qualifying pathogens" that have the potential to pose a serious threat to public health. This final rule issued by the Agency implements a provision of the Generating Antibiotic Incentives Now (GAIN) title of the Food and Drug Administration Safety and Innovation Act (FDASIA).

NTM lung disease is often a chronic condition that can lead to progressive inflammation and lung damage and is characterized by bronchiectasis and cavitary disease. NTM infections often require lengthy hospital stays for medical management. Treatment usually involves multi-drug regimens that can be poorly tolerated and have limited effectiveness, especially in patients with severe disease or in those who have failed prior treatment attempts. These treatments are often associated with drug toxicity and suboptimal outcomes. Achieving NTM culture negativity is one of the objectives of treatment and represents the most clinically important microbiologic endpoint in patients with NTM lung infection.

As infection rates are rising, pulmonary nontuberculous mycobacterial (PNTM) disease represents an emerging public health concern in the United States. NTM are ubiquitous in the environment. Over 80% of pulmonary NTM infections in the US are due to *Mycobacterium avium* complex (MAC). *Mycobacterium avium* Complex is a group of mycobacteria comprising *Mycobacterium* intracellular, *Mycobacterium avium*, and *Mycobacterium* chimaera.

SUMMARY

According to aspects illustrated herein, in an embodiment there is disclosed a fixed-dose combination (FDC) drug product formulated for oral delivery comprising a fixed 158.3 milligram (mg) dose of clarithromycin, a fixed 40.0 milligram (mg) dose of rifabutin, and a fixed 13.3 milligram (mg) dose of clofazimine. In an embodiment, the clofazimine is dispersed in a hydrophilic or hydrophobic carrier. In an embodiment, the carrier is polyethylene glycol. In an embodiment, the drug product further comprises one or more pharmaceutical excipients. In an embodiment, the drug product is a capsule. In an embodiment, the drug product is used for treating non-tuberculosis mycobacterial (NTM) lung disease in a subject in need thereof. In an embodiment, the NTM lung disease is caused by *Mycobacterium avium* Complex (MAC) bacteria.

According to aspects illustrated herein, in an embodiment there is disclosed clarithromycin, rifabutin, and clofazimine in the manufacture of a fixed-dose combination medicament for the treatment of NTM lung disease caused by *Mycobacterium avium* Complex (MAC) bacteria.

According to aspects illustrated herein, in an embodiment there is disclosed a fixed-dose combination (FDC) drug product formulated for oral delivery to a subject having pulmonary *Mycobacterium avium* Complex (MAC) disease substantially as described herein with reference to Table 2.

According to aspects illustrated herein, in an embodiment there is disclosed a method for treating pulmonary *Mycobacterium avium* Complex (MAC) disease in an individual having MAC lung infection that comprises orally administering, once daily, about 475 milligram (mg) of clarithromycin, about 40 milligram (mg) of clofazimine and about 120 milligram (mg) of rifabutin. In an embodiment, the about 475 milligram (mg) of clarithromycin, about 40 milligram (mg) of clofazimine and about 120 milligram (mg) of rifabutin is provided as 3 fixed-dose combination drug products, each drug product comprising a fixed 158.3 milligram (mg) dose of clarithromycin, a fixed 13.3 milligram (mg) dose of clofazimine and a fixed 40.0 milligram (mg) dose of rifabutin.

According to aspects illustrated herein, in an embodiment there is disclosed a method for treating pulmonary *Mycobacterium avium* Complex (MAC) disease in an individual having MAC lung infection that comprises orally administering, twice daily, about 475 milligram (mg) of clarithromycin, about 40 milligram (mg) of clofazimine and about 120 milligram (mg) of rifabutin. In an embodiment, about 40 milligram (mg) of clofazimine and about 120 milligram (mg) of rifabutin is provided as three fixed-dose combination drug products, each drug product comprising a fixed 158.3 milligram (mg) dose of clarithromycin, a fixed 13.3 milligram (mg) dose of clofazimine and a fixed 40.0 milligram (mg) dose of rifabutin.

According to aspects illustrated herein, in an embodiment there is disclosed a method for treating pulmonary *Mycobacterium avium* complex (MAC) disease in a patient having MAC lung infection, the method comprising orally administering to the patient at least three fixed-dose combination drug products, wherein each drug product comprises a fixed 158.3 milligram (mg) dose of clarithromycin, a fixed 13.3 milligram (mg) dose of clofazimine and a fixed 40 milligram (mg) dose of rifabutin, and wherein the administering occurs only on Monday-Wednesday-Friday for a period of time of at least six (6) months. In an embodiment, the administering occurs only once daily on Monday-Wednesday-Friday for a period of time of at least six (6) months, and wherein the patient takes a total daily dose of about 475 milligram (mg) of clarithromycin, about 40 milligram (mg) of clofazimine and about 120 milligram (mg) of rifabutin. In an embodiment, the administering occurs twice daily on Monday-Wednesday-Friday for a period of time of at least six (6) months, and wherein the patient takes a total daily dose of about 950 milligram (mg) of clarithromycin, about 80 milligram (mg) of clofazimine and about 240 milligram (mg) of rifabutin. In an embodiment, the total daily dose of about 950 milligram (mg) of clarithromycin, about 80 milligram (mg) of clofazimine and about 240 milligram (mg) of rifabutin is administered as six fixed-dose combination drug products. In an embodiment, the six fixed-dose combination drug products are administered to the patient in split doses. In an embodiment, the split doses includes three fixed-dose combination drug products and are administered at one point of time during a day and three fixed-dose combination drug products are administered at a later point of time on the same day.

According to aspects illustrated herein, in an embodiment there is disclosed a kit for treating *Mycobacterium avium* Complex (MAC) disease in an individual having MAC lung infection comprising: a supply of fixed-dose combination (FDC) drug products, wherein each of the fixed-dose combination drug products comprise a fixed 158.3 milligram (mg) dose of clarithromycin, a fixed 13.3 milligram (mg) dose of clofazimine and a fixed 40.0 milligram (mg) dose of rifabutin; and instructions for use. In an embodiment, the fixed-dose combination drug products are supplied as capsules. In an embodiment, the instructions for use state to orally three of the fixed-dose combination drug products from the supply two times daily on three days in each week. In an embodiment, the instructions for use state to orally administer three of the fixed-dose combination drug products from the supply in the morning and three of the fixed-dose combination drug products from the supply in the evening on Monday-Wednesday-Friday of a week. In an embodiment, the administration of the FDC drug products should be in conjunction with taking food. In an embodiment, the instructions are a dosing treatment schedule in a readable medium. In an embodiment, the readable medium can include an accompanying pamphlet or similar written information that accompanies the FDC drug products in the kit. In an embodiment, the instructions are a dosing treatment schedule in a storage medium. In an embodiment, the storage medium can include electronic, optical, or other data storage, such as non-volatile memory, for example, to store a digitally-encoded machine-readable representation of such information.

According to aspects illustrated herein, in an embodiment, the patient/subject/individual, prior to being treated, has at least one symptom of MAC lung infection selected from the group consisting of chronic cough, excessive mucous production, fatigue, dyspnea, hemoptysis, fever, night sweats and loss of appetite. In an embodiment, the patient/subject/individual, prior to being treated, does not have HIV1 or HIV2. In an embodiment, the patient/subject/individual, prior to being treated, does not have Hepatitis B or C. In an embodiment, the patient/subject/individual does not have cavitary lung disease. In an embodiment, the patient/subject/individual, prior to being treated, does not require supplemental oxygen use. In an embodiment, the patient/subject/individual, prior to being treated, does not have severe renal impairment. In an embodiment, the patient/subject/individual does not have a history of QT prolongation or ventricular arrhythmia. In an embodiment, the administration period is continued for an amount of time sufficient to result in a negative sputum culture for MAC. In an embodiment, the amount of time sufficient to result in a negative sputum culture for MAC is from 1 month to 8 months. In an embodiment, the method further comprises, prior to the administering step, confirming that the patient has a positive sputum culture for MAC. In an embodiment, the patient is an adult.

In an embodiment, during the administration period or subsequent to the administration period, the patient/subject/individual exhibits an NTM culture conversion to negative. In an embodiment, during the administration period or subsequent to the administration period, the patient/subject/individual walks an increased number of meters in the 6 minute walk test (MWT), as compared to the number of meters walked by the patient/subject/individual prior to undergoing the treatment method. In an embodiment, prior to the treating, the patient/subject/individual was unresponsive to a different MAC therapy. In an embodiment, prior to the treating, the patient/subject/individual was unresponsive to an American Thoracic Society/Infectious Disease Society of America (ATS/IDSA) MAC guideline-based therapy (GBT). In an embodiment, prior to the treating, the patient/subject/individual was unresponsive to the ATS/IDSA MAC GBT for at least 6 months. In an embodiment, the increased number of meters walked by the patient/subject/individual is at least about 5 meters. In an embodiment, the increased number of meters walked by the patient/subject/individual is at least about 20 meters. In an embodiment, the increased number of meters walked by the patient/subject/individual is at least about 25 meters. In an embodiment, the increased number of meters walked by the patient/subject/individual is from about 5 meters to about 50 meters.

DETAILED DESCRIPTION

Figure 1:
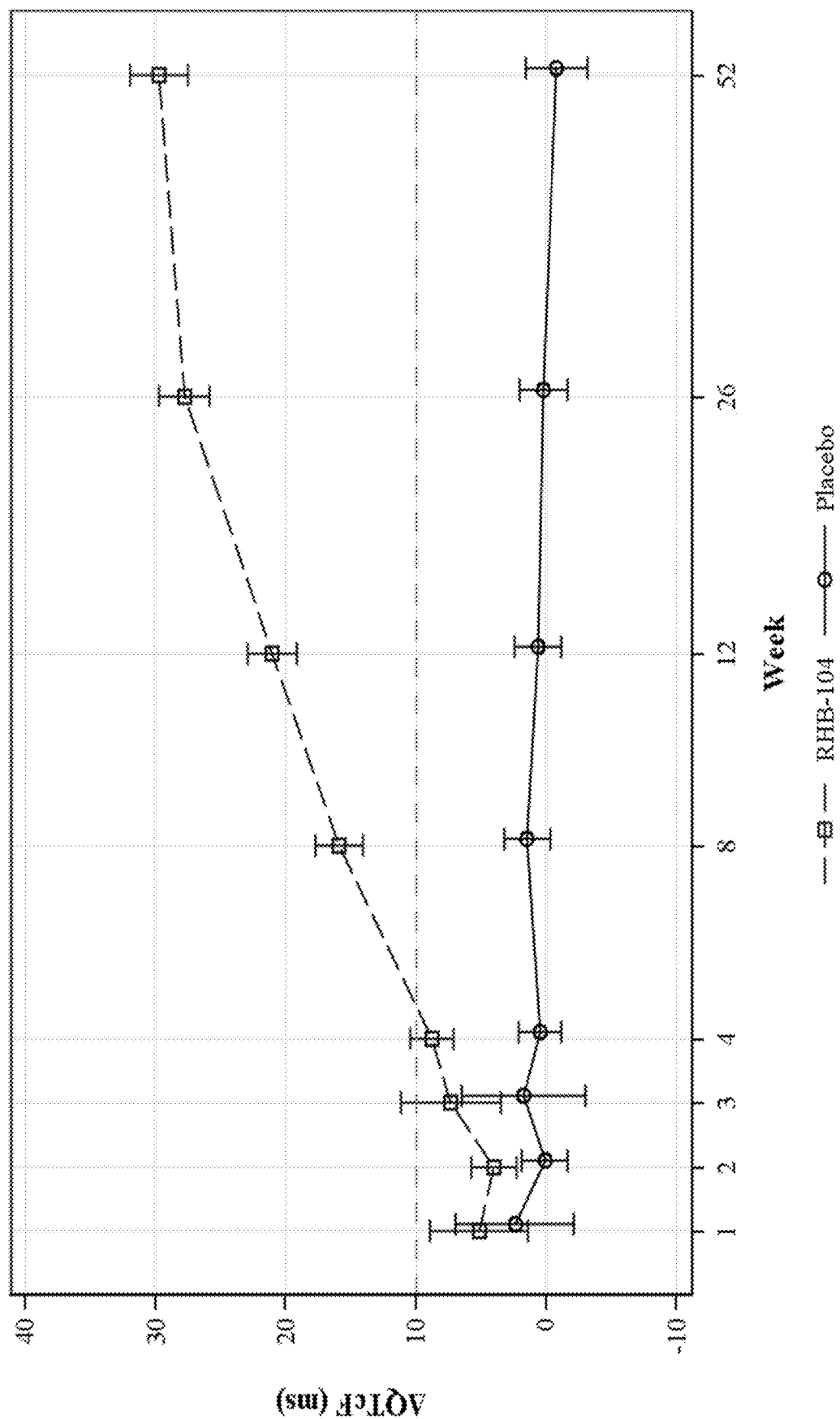
FIG. 1 is a graph showing the change-from-baseline QTcF (ΔQTcF) across visit (QT/QTc analysis set) in a Phase 3 clinical study (the "MAP Study") testing the efficacy and safety of a FDC product comprising 3 antibiotics, CLR:CFZ:RFB (each FDC comprising 95 mg:10 mg:45 mg) "RHB-104" given as 10 capsules daily for 52 weeks in the treatment of adults with moderate to severely active Crohn's disease. ΔQTcF: Baseline-adjusted change in QTcF interval; Least Square (LS) means and 90% Confidence Interval (CI) based on a linear mixed-effects model.

NTM lung disease or pulmonary NTM disease is a serious infection caused by bacteria that are common in the environment and can cause lung damage. The most common species of NTM is *Mycobacterium avium* complex (MAC). Eight out of ten NTM infections in the United States are caused by MAC. The effect of the individual antibiotics, clarithromycin (CLR), rifabutin (RFB) and clofazimine (CFZ), as well as two-drug combinations, has been described in several nonclinical models of NTM systemic and lung infection.

On an individual component level, preclinical literature suggests that clarithromycin doses of approximately 50 mg/kg/day to 100 mg/kg/day result in efficacy in both systemic and lung infection mouse models. Similarly, rifabutin and clofazimine doses of approximately 10-20 mg/kg/day suggest efficacy in mouse models of lung infection. As the systemic exposure of the drugs was not reported following the respective treatments, translation to an effective dose in humans can be performed by conversion to human equivalent doses (HEDs) based on body surface area scaling. A divisor of 12.3 is used to convert mg/kg/day dosing in mice to obtain a human equivalent dose, see Table 1 (CDER, FDA Guidance, 2005). See Table 1 below.

TABLE 1

Human-Equivalent Dose Conversions of CLR, CFZ, RFB from Selected mg/kg/day Doses in Mice

| Drug Component | Effective Dose (mg/kg/day) | Human Equivalent Daily Dose (mg, based on a 60 kg Human) |
|---|---|---|
| Clarithromycin | 50-100 | 244-488 |
| Rifabutin | 10 | 49 |
| Clofazimine | 20 | 98 |

To achieve the same mg dose(s) over a period of a week, these doses translate to approximately 570 mg to 1,140 mg per day for clarithromycin, 114 mg per day for rifabutin and 229 mg per day for clofazimine, when administered on three of seven days per week (M-W-F).

The present disclosure provides triple antibiotic fixed-dose combination (FDC) drug products for effectively treating a pulmonary MAC disease in a patient in need thereof, by which adverse effects are minimized during treatment. Pre-clinical data (literature, in-vitro models and in vivo models) demonstrate that each of the three antibiotic components contribute to the anti-MAC activity in the FDC of the present invention. In in vitro models of MAC infection, the three-drug combination exhibited the steepest kill and reduction in bacterial burden when compared to clarithromycin alone or clarithromycin, two-drug combination. In vivo models of MAC lung infection in mice further support the contribution of each component. While the two-drug combination of clofazimine and three-drug combination performed similarly in lung, in individual animals, the three-drug combination exhibited the largest reduction in bacterial load. Moreover, in mice inoculated with a resistant strain to clarithromycin, there was a rank order reduction in lung bacterial load both two-drug combination and the three-drug combinations with the best response observed with the three-drug treatment, producing mean bacterial load below that observed baseline.

Whilst considering the potential range of efficacious doses, the safety profile of each antibiotic component was evaluated in terms of the dose and/or exposure with safety/tolerability considerations. The doses were chosen to minimize the risk of commonly associated adverse effects, in particular the potential for QTc prolongation, which was discovered in clinical data of a prior art FDC, RHB-104, discussed below. In particular, rifabutin and clofazimine doses were carefully selected to mitigate the risk of serious adverse events (e.g. uveitis for rifabutin and QTc prolongation for clofazimine). In conclusion, the components and doses for the FDC of the present invention, and the specific dosing regimen disclosed herein, were selected based on the pre-clinical evaluation, PK modelling and clinical experience with each of the active components and their combination, to maximize therapeutic effectiveness against MAC while minimizing potential side-effects for optimal risk-benefit.

As used herein, "MAC lung disease", "pulmonary *Mycobacterium avium* Complex (PMAC) disease", "NTM lung disease" or "pulmonary nontuberculous mycobacterial (PNTM) disease" are used interchangeably.

As used herein, the terms "about" and "approximately" are defined as being close to as understood by one of ordinary skill in the art, and in one non-limiting embodiment the terms are defined to be within 10%, within 5%, within 1%, or within 0.5%. As used herein, the term "about" is used to indicate that a value includes the standard deviation of error for the device and/or method being employed to determine the value.

As used herein, "refractory MAC lung disease" is defined as patients who did not achieve negative sputum cultures after a minimum of 6 consecutive months of a multidrug background regimen therapy.

A "dosage regimen" or "dosing regimen" includes a treatment regimen based on a determined set of doses. In an embodiment, the disclosure describes a dosing regimen for the treatment of MAC lung disease, wherein a total of about 950 mg clarithromycin, about 240 mg rifabutin and about 80 mg clofazimine are administered daily as six (6) FDC products administered in two divided doses (i.e., 3 FDC products administered twice per day) t.i.w. (three times per week) on Monday, Wednesday, and Friday (M-W-F).

As used herein, BID, TIW refers to twice a day on Monday, Wednesday, Friday.

As used herein, "CLR" refers to clarithromycin, "CFZ" refers to clofazimine, and "RFB" refers to rifabutin.

As used herein, the terms "fixed-dose combination" (FDC) and "unit dose" are defined as pharmaceutical compositions comprising predetermined amounts (fixed dosage strengths) of the active ingredients CLR, CFZ and RFB. Typically, the FDC is an oral capsule that comprises therapeutically effective amounts of CLR, CFZ and RFB and one or more pharmaceutical excipients. As used herein, a "total daily dose" is an amount given or prescribed in a 24 hr period. In an embodiment, the FDC products of the present disclosure are administered to a subject in split doses. As used herein, a "split dose" is the division of a total daily dose into two or more doses. FDC in accordance with the invention may be prepared, packaged, and/or sold in bulk as a plurality of unit doses.

As used herein, "RHB-104" refers to a FDC product including the following predetermined amounts of the active ingredients CLR:CFZ:RFB, 95 mg:10 mg:45 mg. Such a FDC of antibiotics was first taught in International Patent Application No. PCT/AU09/000129, filed on Feb. 5, 2009. Application No. PCT/AU09/000129 described use of the FDC in the treatment of Inflammatory Bowel Diseases, which is incorporated herein in its entirety.

In an embodiment, a FDC of the present invention includes the following predetermined amounts of the active ingredients CLR:CFZ:RFB, 158.3 mg:13.3 mg:40 mg. In an embodiment, the clofazimine is dispersed in a hydrophilic or hydrophobic carrier such as a polyethylene glycol (PEG), polyvinylpyrrolidone (PVP) hydroxypropyl methylcellulose, gums, sugar, mannitol, urea, and colloidal silicon dioxide, forming a clofazimine-polymer solid dispersion. In an embodiment, the hydrophilic carrier is a PEG having an average molecular weight of between 200-20,000, including between 1000-15,000, between 5,000-12,000, and between 7,000-9,000. In an embodiment, the PEG has an average molecular weight of 8,000. In an embodiment, clofazimine is dispersed in PEG to form a PEG/clofazimine dispersion and subsequently mixed with clarithromycin and rifabutin.

Table 2 provides an embodiment of a composition of a FDC of the present invention. In an embodiment, the FDC comprises one or more pharmaceutical excipients that are used in tablets and capsules, including, but not limited to, disintegrants, lubricants, anticaking agents, coloring agents, binders, diluents or fillers, antioxidants, glidants, wetting agents, and preservatives (e.g., antimicrobial preservatives).

TABLE 2

An embodiment of a FDC of the present disclosure

| Component and Quality Standard | Function | Strength (label claim) | |
|---|---|---|---|
| | | Quantity per unit | % |
| Clofazimine, USP/EP | Active | 13.3 | 2.54 |
| Polyethylene Glycol 8000 granular, USP/EP | Dispersing Agent | 39.4 | 7.50 |
| Polysorbate 80 USP/EP | Wetting Agent | 5.3 | 1.00 |
| Microcrystalline Cellulose 200 USP/EP | Diluent | 249.3 | 47.49 |
| Rifabutin USP/EP | Active | 40.0 | 7.62 |
| Clarithromycin USP/EP | Active | 158.3 | 30.16 |

TABLE 2-continued

An embodiment of a FDC of the present disclosure

| Component and Quality Standard | Function | Strength (label claim) | |
|---|---|---|---|
| | | Quantity per unit | % |
| Sodium Lauryl Sulfate USP/EP | Wetting Agent | 11.5 | 2.20 |
| Magnesium Stearate, vegetable grade (NF/Ph. Eur. + In-House) | Lubricant | 7.9 | 1.50 |
| Hard Gelatin Capsule, size 0 (Mfg Std) | Capsule | 94.0 | n/a |
| Total | — | 619.0 | 100.0% |

The dosing regimen of a FDC product of the present invention for the treatment of NTM lung disease is discussed below and provides total daily doses of about 950 mg (949.8 mg) per day for clarithromycin, 240 mg per day for rifabutin and about 80 mg (79.8 mg) per day for clofazimine, when administered on three of seven days per week (i.e. Monday, Wednesday and Friday, [M-W-F]). When normalized to a daily dose, the dosing regimen for a FDC product of the present invention for the treatment of MAC lung disease is equivalent to approximately 43%, 23% and 34% of the daily doses of CLR, RFB and CFZ used in the FDC RHB-104 for Crohn's disease, respectively.

In an embodiment, the total daily dose is titrated up over the first 2 weeks and remains stable thereafter. For example, for weeks 1 and 2, the patient can take a total of 3 FDC products on M-W-F. From week 3 on, the patient can take a total of 6 FDC products on M-W-F.

The term "treating" includes: (1) preventing or delaying the appearance of clinical symptoms of the state, disorder or condition developing in the subject that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a subject to be treated is either statistically significant or at least perceptible to the subject or to the physician.

The term "antibacterial" is art-recognized and refers to the ability of the compounds of the present invention to prevent, inhibit or destroy the growth of microbes of bacteria.

"Effective amount" means an amount of an antibiotic used in the present invention sufficient to result in the desired therapeutic response.

The "Quality of Life Questionnaire-Bronchiectasis (QoL-B)" is a self-administered, patient-reported outcome (PRO) measure assessing symptoms, functioning and health-related quality of life for patients with bronchiectasis, containing 37 items on 8 scales (Respiratory Symptoms, Physical, Role, Emotional and Social Functioning, Vitality, Health Perceptions and Treatment Burden).

The safety and effectiveness of a FDC disclosed in PCT/AU09/000129 were evaluated in a randomized, double-blind, controlled Phase 3 study of RHB-104 in adults with Crohn's disease ("MAP Study"). More specifically, the FDC used in the MAP Study was RHB-104 and was administered according to a dosing regimen which consisted of administering each day for a 1 week period of treatment a total daily dose of the following amounts of actives: (i) 90 mg rifabutin, (ii) 190 mg clarithromycin, and (iii) 20 mg clofazimine, administered as 2 capsules of RHB-104 daily; for a 1 week period of treatment (e.g., week 2 of treatment) a total daily dose of the following amounts of actives: (i) 180 mg rifabutin, (ii) 380 mg clarithromycin, and (iii) 40 mg clofazimine, administered as 4 capsules of RHB-104 daily; for a 1 week period of treatment (e.g., week 3 of treatment) a total daily dose of the following amounts of actives: (i) 270 mg rifabutin, (ii) 570 mg clarithromycin, and (iii) 60 mg clofazimine, administered as 6 capsules of RHB-104 daily; for a 1 week period of treatment (e.g., week 4 of treatment) a total daily dose of the following amounts of actives: (i) 360 mg rifabutin, (ii) 760 mg clarithromycin, and (iii) 80 mg clofazimine, administered as 8 capsules of RHB-104 daily; for the remainder of the treatment schedule a total daily dose of the following amounts of actives: (i) 450 mg rifabutin, (ii) 950 mg clarithromycin, and (iii) 100 mg clofazimine, administered as 10 capsules of RHB-104 daily. Thus, following a 4-week dose titration period, the target dosing regimen in CD of 5 capsules twice daily (BID) provided total daily doses of 950 mg per day for clarithromycin, 450 mg per day for rifabutin, and 100 mg per day for clofazimine.

In the MAP Study, RHB-104 administered according to the dosing regimen described above for 52 weeks successfully met both its primary endpoint of clinical remission (CDAI <150) at week 26 (36.7% vs. 22.4%, p=0.0048) and key secondary and other efficacy endpoints of clinical response at week 26 (p=0.016), early clinical remission at week 16 (p=0.015), clinical remission at weeks 16 and 52 (25.9% vs. 12.1%, p=0.0016) and, notably, durable clinical remission on all visits, weeks 16 through 52 (18.7% vs. 8.5%, p=0.0077, RHB-104 vs. placebo, respectively). Consistent treatment effects and meaningful clinical benefit strongly favoring RHB-104 as compared to placebo was demonstrated in subgroups of patients receiving baseline standard-of-care therapies, including immunomodulators (39% vs. 20%), corticosteroids (36% vs. 20%) and anti-TNF agents (36% vs. 17%). RHB-104 was found to be generally safe and well tolerated.

QT prolongation is a measure of delayed ventricular repolarization, which means the heart muscle takes longer than normal to recharge between beats. It is an electrical disturbance which can be seen on an electrocardiogram (ECG), which shows rapid irregular QRS complexes. Excessive QT prolongation can trigger tachycardias such as Torsades de Pointes (TdP), which is translated from French as "twisting of the peaks" because the complexes appear to undulate, or twist around, the EKG baseline. TdP can be acquired by inheritance of a congenital long QT syndrome, or more commonly from the ingestion of a pharmacologic drug. On an ECG, the QT interval represents the summation of action potentials in cardiac muscle cells, which can be caused by an increase in inward current through sodium or calcium channels, or a decrease in outward current through potassium channels. By binding to and inhibiting the "rapid" delayed rectifier potassium current protein, certain drugs are able to decrease the outward flow of potassium ions and extend the length of phase 3 myocardial repolarization, resulting in QT prolongation.

A QT interval measurement begins from the start of the Q wave to the end of the T wave. The value is an indication of the time it takes for a ventricle from the beginning of a contraction to the end of relaxation. The value for a normal QT interval is similar in males and females from birth up to adolescence. During infancy, a normal QTc is defined as 400+/−20 milliseconds. Before puberty, the 99th percentile of QTc values is 460 milliseconds. After puberty, this value increases to 470 milliseconds in males and 480 milliseconds in females. Most patients with drug-induced QT prolongation are asymptomatic and are diagnosed solely by ECG in association with a history of using medications known to cause QT prolongation. A minority of patients are symptomatic and typically present with one or more signs of arrhythmia, such as lightheadedness, syncope, or palpitations. If the arrhythmia persists, patients may experience sudden cardiac arrest.

In the analysis of the complete safety information for the MAP Study, a top-line ECG monitoring report demonstrated evidence of progressive prolongation of the QTcF interval across visits, with the largest mean difference observed the largest AQTcF of 29.8 ms observed at Week 52, see FIG. 1. In contrast, changes were very small in placebo subjects. Mean placebo-corrected AQTcF (ΔΔQTcF) therefore increased from 2.8 ms at Week 1 to 30.6 ms at Week 52. While none of these QT abnormalities resulted in adverse cardiac events, it might be suggested that RHB-104, at the dosing regimen and schedule tested, should be avoided in patients with pre-existing heart disease, history of ventricular arrhythmias or with metabolic abnormalities such as hypokalemia. According to FDA guidance, in clinical trials, a prolongation of QTc >500 ms or an increase in baseline above 30 ms has been a threshold of particular concern. Establishing the relationship of drug concentration to changes in QT/QTc interval may provide additional information to assist the planning and interpretation of studies assessing cardiac repolarization.

QT prolongations are undesirable, and methods to minimize these effects would be valuable for maximizing the safety of FDC products of the present disclosure and minimizing associated monitoring requirements during treatment with the therapy. The regimen of FDC products disclosed herein, for treating MAC lung disease, has been sufficiently designed to mitigate the risk of clinically important QTc prolongation whilst maintaining the clinical efficacy of the combination treatment, as described in detail in the Examples section of this application.

Oral administration of FDC products of the present disclosure for a sufficient period of time results in a therapeutic response that can be any response that a user (e.g., a clinician) will recognize as an effective response to the therapy. The therapeutic response will generally be a reduction, inhibition, delay or prevention in growth of or reproduction of one or more NTM, or the killing of one or more NTM. A therapeutic response may also be reflected in an improvement in pulmonary function, for example forced expiratory volume in one second ($FEV_1$). In one embodiment, where a patient is treated for an NTM lung infection, the therapeutic response is measured as the change from baseline on the full semi quantitative scale for mycobacterial culture or an improvement in the distance walked in the 6 minute walk test (6MWT). It is further within the skill of one of ordinary skill in the art to determine appropriate treatment duration, appropriate doses, and any potential combination treatments, based upon an evaluation of therapeutic response.

The NTM lung infection treatable by the methods and compositions described herein, in one embodiment, is *M. avium* complex (MAC) (*M. avium* and *M. intracellulare*).

The methods provided herein, in one embodiment, comprise administering to a patient in need thereof one of the compositions described herein for an administration period comprising at least one 1 month, 2 months, 3 months, 4 months, 5 months or 6 months. In one embodiment, an administration period is followed by a period where no composition is administered (referred to as "off period"), which is followed by another administration period. The off period, in one embodiment is about 1 month, about 2 months, about 3 months, about four months, about five months or about 6 months.

In one embodiment, the administration period is from about 15 days to about 400 days, e.g., from about 45 days to about 300 days, or from about 45 days to about 270 days, or from about 80 days to about 200 days. In one embodiment, the administration period comprises administration of the composition to a patient in need thereof in a twice daily dosing session.

In one embodiment, an administration period is followed by an off period from about 15 to about 200 days, for example, from about 15 days to about 150 days, or from about 15 days to about 75 days, from about 15 days to about 35 days, or from about 20 days to about 35 days, or from about 25 days to about 75 days, or from about 35 days to about 75 days or from about 45 days to about 75 days. In another embodiment, the off period is about 28 days or about 56 days. In other embodiments, the off period is about 50, 51, 52, 53, 54, 55, 56, 57, 58, 59 or 60 days, while in other embodiments, the off period is about 56 days.

In one embodiment, the patient in need thereof is administered FDC products of the present invention in a treatment cycle comprising an administration period and an off period. In a further embodiment, the treatment cycle is implemented at least once. In a further embodiment, the treatment cycle is repeated at least twice, for example, two, three, four, five, six, seven, eight, nine or ten times. In another embodiment, the treatment cycle is repeated at least three times, for example, at least three, at least four, at least five or at least six times.

In an embodiment, the methods provided herein are implemented for the treatment or prophylaxis of one or more NTM pulmonary infections in a cystic fibrosis patient.

In one embodiment, the patient in need of treatment of the NTM pulmonary infection is a bronchiectasis patient. In one embodiment, the bronchiectasis is non-Cystic Fibrosis (CF) bronchiectasis. In another embodiment, the bronchiectasis is associated with CF in a patient in need of treatment.

In another embodiment, the patient in need of treatment of the NTM pulmonary infection is a COPD patient. In yet another embodiment, the patient in need of treatment of the NTM pulmonary infection is an asthma patient.

In one embodiment, a patient in need of treatment with one of the methods described herein is a Cystic Fibrosis patient, a bronchiectasis patient, a ciliary dyskinesia patient, a chronic smoker, a chronic obstructive pulmonary disorder (COPD) patient, or a patient who has been previously non-responsive to treatment. The pulmonary NTM infection, in one embodiment, is MAC, *M. kansasii, M. abscessus*, or M. fortuitum. In a further embodiment, the pulmonary NTM infection is a MAC infection.

A patient subjected to the methods described herein, in one embodiment, has a comorbid condition. For example, in one embodiment, the patient in need of treatment with one of the methods described herein has diabetes, mitral valve disorder (e.g., mitral valve prolapse), acute bronchitis, pulmonary hypertension, pneumonia, asthma, trachea cancer, bronchus cancer, lung cancer, cystic fibrosis, pulmonary fibrosis, a larynx anomaly, a trachea anomaly, a bronchus anomaly, aspergillosis, HIV or bronchiectasis, in addition to the pulmonary NTM infection.

In one embodiment, a patient subjected to one of the NTM methods described herein exhibits an NTM culture conversion to negative during the administration period of composition, or after the administration period has concluded. The time to conversion, in one embodiment, is about 10 days, or about 20 days or about 30 days or about 40 days, or about 50 days, or about 60 days, or about 70 days, or about 80 days, or about 90 days, or about 100 days or about 110 days or about 120 days or about 130 days or about 140 days of about 150 days or about 160 days of about 170 days or about 180 days or about 190 days or about 200 days or any value therebetween. In another embodiment, the time to conversion is from about 20 days to about 200 days, from about 20 days to about 190 days, from about 20 days to about 180 days, from about 20 days to about 160 days, from about 20 days to about 150 days, from about 20 days to about 140 days, from about 20 days to about 130 days, from about 20 days to about 120 days, from about 20 days to about 110 days, from about 30 days to about 110 days, or from about 30 days to about 100 days.

In some embodiments, the patient experiences an improvement in lung function for at least 15 days after the administration period ends, as compared to the $FEV_1$ of the patient prior to treatment. For example, the patient may experience an increase in $FEV_1$, an increase in blood oxygen saturation, or both. In some embodiments, the patient has an $FEV_1$ (after the administration period or treatment cycle) that is increased by at least 5% over the $FEV_1$ prior to the administration period. In other embodiments, $FEV_1$ is increased by 5 to 50% over the $FEV_1$ prior to the administration period. In other embodiments, $FEV_1$ is increased by 25 to 500 mL over $FEV_1$ prior to the administration period. In some embodiments, blood oxygen saturation is increased by at least 1% over oxygen saturation prior to the administration period.

In one embodiment, the 6-minute walk test (6MWT) is used to assess the effectiveness of the treatment methods provided herein. The 6MWT is used for the objective evaluation of functional exercise capacity and is a practical, simple test that measures the distance that a patient can walk in a period of 6 minutes (see American Thoracic Society. (2002). Am J Respir Crit Care Med. 166, pp. 111-117, incorporated by reference herein in its entirety for all purposes).

In one embodiment, a patient subjected to one of the NTM methods described herein exhibits an increased number of meters walked in the 6MWT, as compared to prior to undergoing the treatment method. The increased number of meters walked in the 6MWT, in one embodiment, is about 5 meters, about 10 meters, about 15 meters, about 20 meters, about 25 meters, about 30 meters, about 35 meters, about 40 meters, about 45 meters, or about 50 meters. In another embodiment, the increased number of meters walked in the 6MWT is at least about 5 meters, at least about 10 meters, at least about 15 meters, at least about 20 meters, at least about 25 meters, at least about 30 meters, at least about 35 meters, at least about 40 meters, at least about 45 meters, or at least about 50 meters. In yet another embodiment, the increased number of meters walked in the 6MWT is from about 5 meters to about 50 meters, or from about 5 meters to about 40 meters, or from about 5 meters to about 30 meters or from about 5 meters to about 25 meters.

In another embodiment, a patient subjected to one of the NTM methods described herein exhibits a greater number of meters walked in the 6MWT, as compared to a patient undergoing a non-liposomal aminoglycoside treatment. The greater number of meters walked in the 6MWT, as compared to a patient undergoing a non-liposomal aminoglycoside treatment, in one embodiment, is about 5 meters, about 10 meters, about 15 meters, about 20 meters, about 25 meters, about 30 meters, about 35 meters, about 40 meters, about 45 meters, about 50 meters, about 60 meters, about 70 meters or about 80 meters. In another embodiment, the greater number of meters walked in the 6MWT is at least about 5 meters, at least about 10 meters, at least about 15 meters, at least about 20 meters, at least about 25 meters, at least about 30 meters, at least about 35 meters, at least about 40 meters, at least about 45 meters, or at least about 50 meters. In yet another embodiment, the greater number of meters walked in the 6MWT is from about 5 meters to about 80 meters, or from about 5 meters to about 70 meters, or from about 5 meters to about 60 meters or from about 5 meters to about 50 meters.

In one embodiment, a composition provided herein is administered to a patient in need of treatment of an NTM lung disease with an additional therapy.

In one embodiment, a composition provided herein is administered to a patient in need of treatment of an NTM lung disease with one or more additional therapeutic agents. The one or more additional therapeutics agents in one embodiment, is administered orally. In another embodiment, the one or more additional therapeutics agents in one embodiment, is administered intravenously. In yet another embodiment, the one or more additional therapeutics agents in one embodiment, is administered via inhalation.

The one or more additional therapeutic agents in one embodiment, is an aminoglycoside. In another embodiment, the one or more additional therapeutic agents is a quinolone. In a further embodiment, the quinolone is a fluoroquinolone. In another embodiment, the quinolone is ciprofloxacin, levofloxacin, gatifloxacin, enoxacin, levofloxacin, ofloxacin, moxifloxacin, trovafloxacin, or a combination thereof. In another embodiment, a composition provided herein is administered to a patient in need of treatment of an NTM lung disease with one or more additional therapeutic agents, and the one or more additional therapeutic agents is ethambutol, isoniazid, cefoxitin or imipenem or a combination thereof.

In a related aspect, provided herein is a pharmaceutical kit including a container comprising a plurality of unit dosage forms of the present invention and instructions for use. In an embodiment, the instructions may instruct the patient to take three (3) FDC capsules of the present disclosure two times within a 24 hour time period, wherein a total of 6 capsules should be administered three times per week. According to an embodiment of the present disclosure, use of the above pharmaceutical composition or pharmaceutical kit for preparing a medicament for treating pulmonary *Mycobacterium avium* Complex (MAC) disease is provided. In an embodiment, a pharmaceutical kit is a bottle comprising between 100 and 110 FDC capsules, and more particularly a bottle comprising 108 FDC capsules of the present disclosure.

A FDC of the present invention can contain one of more excipients, such as disintegrants, lubricants, anticaking agents, binders, antioxidants, glidants and preservatives (e.g., antimicrobial preservatives).

EXAMPLES

The present invention is further illustrated by reference to the following Examples. However, it should be noted that these Examples, like the embodiments described above, are illustrative and are not to be construed as restricting the scope of the invention in any way.

Example 1—CFZ, CLR and RFB in Static Time-Kill Assays

In vitro, efficacy was studied in static time-kill kinetics assays (at 2×minimum inhibitory concentration [MIC]), intended to mirror a desired peak serum concentration for all three antibiotics using an established assay. All experiments were performed with a starting inoculum of 5.5 $\log_{10}$ CFU/ml MAC bacteria, higher than the bacterial load expected in the airway secretions of patients with mild nodular-bronchiectatic disease due to MAC. RFB, CFZ, and CLR, as single drugs, exhibited bacteriostatic activity, however after 5-7 days, their effect was abrogated by the emergence of resistance. All two-drug combinations (i.e. RFB-CFZ, RFB-CLR, CFZ-CLR) exhibited faster killing than all single drugs, which was not abrogated by resistance during the first 10 days.

The three-drug regimen, CFZ:CLR:RFB exhibited the fastest and most extensive killing; it is the only combination that exhibited >3 log CFU killing. Its killing effect continued until day 10 and was not abrogated by the emergence of resistance. All three drugs in combination exhibit conservable accumulation in macrophages where mycobacteria reside and replicate, in concentrations 20-200 times the concentration in serum ($C_{max}$) and thus the intracellular killing of MAC is likely more extensive than the killing observed in this in vitro experiment.

Example 2—Hollow Fiber Experiments Support the Contribution of CFZ, CLR and RFB Administered in a Three-Drug Combination Vs. One- and Two-Drug Combination The anti-mycobacterial effects of CLR, CFZ, and RFB was evaluated in the hollow fiber system model of MAC (HFS-MAC), which recapitulates the intrapulmonary concentrations of these antibiotics. The HFS-MAC allows for an assessment of the contribution of individual drug components in terms of anti-mycobacterial effects and enables exploration of potential synergy, additivity, or antagonism of different doses of drugs and combination regimens on the log-phase growth of intracellular MAC, for both microbial kill and resistance suppression.

A two-part investigation was conducted to assess the contribution of components of various FDC products comprising CLR, CFZ, and RFB in terms of depth and rate of MAC kill and suppression of the emergence of resistance. The anti-MAC activity of each antibiotic component was evaluated as one-drug alone; as two-drug combinations and the three-drug combination. For each combination (singlet, doublet or triplet), the drug concentrations were sampled from the HF fluid bathing MAC-infected cells. This fluid is believed to represent interstitial fluid (for lung tissue infection), or epithelial lining fluid (ELF), where MAC-infected macrophages reside in the lung airways. Anti-MAC activity was evaluated by kill slopes defined as the kill rate constant (and the half-life of kill [reciprocal of the kill rate constant]) as well as the maximum kill, defined as the maximum reduction in MAC CFUs and compared between the different antibiotic combinations.

Hollow Fiber System Model of MAC

Figure 2:
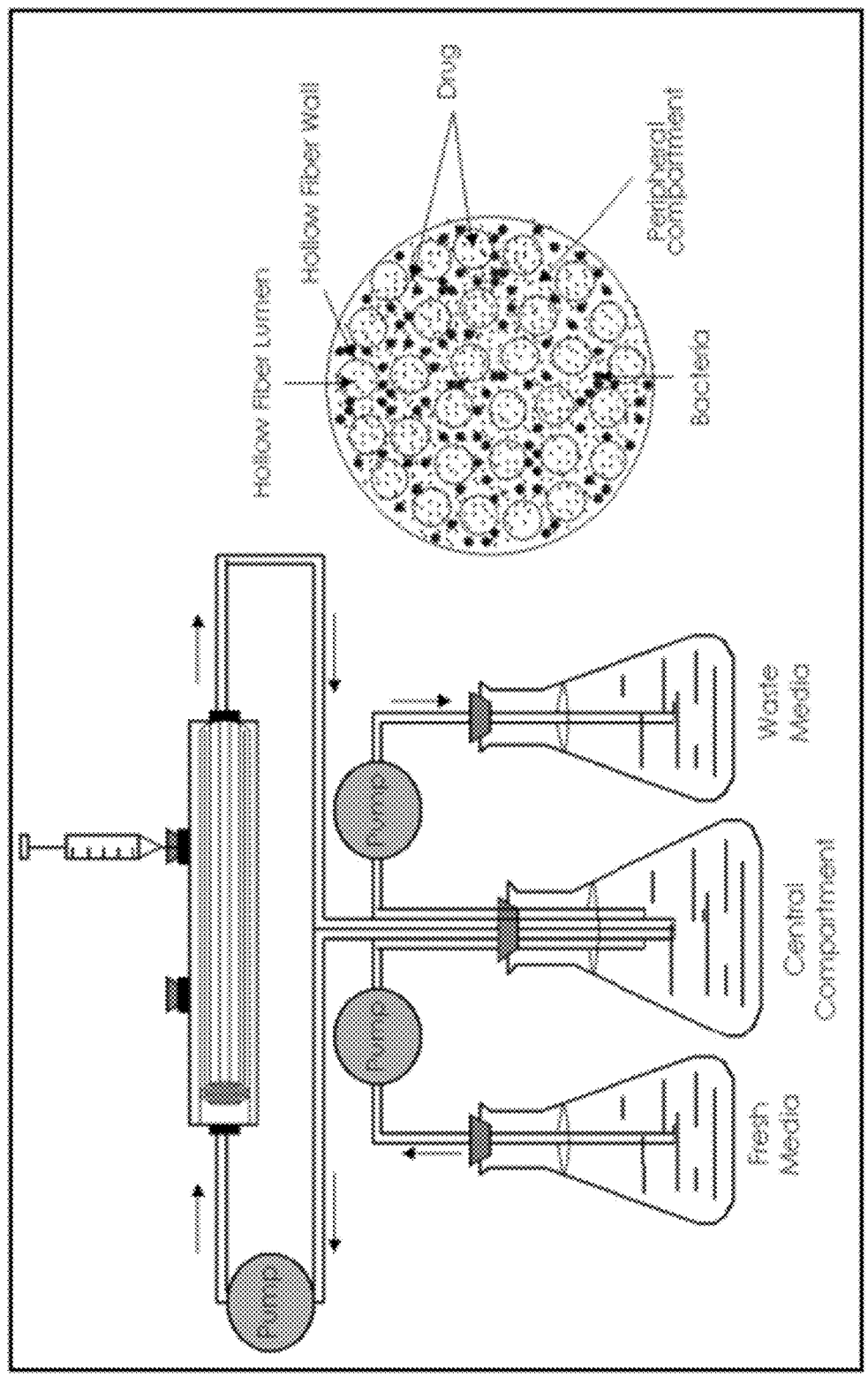
FIG. 2 is a schematic of the hollow fiber system model of MAC.

MAC was grown into log-phase for 4 days, parallel with cultivation of THP-1 monocytes. The THP-1 cells were then infected with MAC overnight at a multiplicity of infection of 1:1. The THP-1 cells were washed to remove extracellular bacteria, and 20 mL of 1×10⁶ (6.0 $\log_{10}$) cells/mL were inoculated into each HFS-MAC on Study Day 0. In the HFS-MAC cartridge, hollow fibers are semipermeable capillary tubes encased in a plastic cartridge, as shown in FIG. 2. The peripheral compartment is the abluminal hollow fibers space that is also enclosed by the plastic, while the intraluminal space and flow path form the central compartment. The MAC-infected monocytes and the bacteria are too big to pass through the semipermeable fibers while small molecules such as CLR, CFZ, and RFB, which are circulating in the central compartment, diffuse rapidly into the peripheral compartment where the infected monocytes are housed. The antibiotics are administered into the central compartment via computerized syringe pumps. Fresh media is added to the circulating media in the central compartment and used media removed in an isovolumetric manner at rates that create a dilutional system with a half-life ($t_{1/2}$) that mimics the lung concentration-time profiles (PK) of the test drugs. Repetitive sampling of the central and peripheral compartments allows for determination that the intended concentration-time profiles were achieved, and to identify intracellular MAC burden, and acquired drug resistance. Table 3 lists the chemicals and reagents used in the experiments.

TABLE 3

Growth media

| Reagent | Supplier | Storage |
|---|---|---|
| MBSAT-20 | REMEL | Ambient |
| Middlebrook 7H9 | REMEL | Ambient |
| BSA | SIGMA | 4° C. |

Table 4 lists the MAC strain and human cell lines used in the studies. The MAC strain used in the HFS-MAC studies was ATCC strain 700898. The study center also had 5 well-characterized clinical strains that have undergone whole-genome sequencing and habituation to the HFS-MAC. Stock cultures of MAC were stored at −80° C. in Middlebrook 7H9 broth with 10% OADC and 10% glycerol. THP-1 monocytes were stored in liquid nitrogen and have been habituated for the HFS-MAC growth conditions.

TABLE 4

Listing of the MAC strain and human cell lines

| Cell Line | Comment | Clarithromycin MIC mg/L | Rifabutin MIC [mg/L] | Clofazimine MIC [mg/L] |
|---|---|---|---|---|
| MAC (ATCC 700898) | Laboratory strain | 0.25 | 0.0625 | |
| Clinical strains | Clinical strain #1 | 0.125 | 0.125 | 0.25 |
| | Clinical strain #2 | 0.5 | 0.125 | 0.25 |
| | Clinical strain #3 | 32 | 0.125 | 0.25 |
| | Clinical strain #4 | 0.25 | 2.0 | 0.25 |
| | Clinical strain #5 | 0.125 | 0.125 | 0.25 |
| THP-1 monocytes | HFS-MAC habituated THP-1 cells | | | |

The Mycobacterial Growth Indicator Tube (MGIT) assay was performed using the BACTEC™ MGIT™ 960 Mycobacterial Detection System. Data were collected using EPi-Center software. LC-MS/MS analysis was performed using Waters Acquity UPLC connected to a Waters Xevo TQ mass spectrometer (Milford, Mass.). Data were collected using MassLynx version 4.1 SCN810 software.

In an initial set of experiments (Part 1), triple combination (clarithromycin, rifabutin and clofazimine) was associated with the best kill rates and addition of clofazimine to a clarithromycin backbone regimen, mitigated the emergence of clarithromycin resistance. Part 1 demonstrated that the maximal response was achieved with a CLR target of approximately 60 mg·h/L and this AUC was estimated to be approximately 2-3-fold greater than what would be tolerated from the clarithromycin clinical experience. Therefore, lower target clarithromycin exposures were tested to understand the exposure-response relationship for the macrolide backbone of the regimen.

The systemic exposure of CLR, CFZ and RFB components as part of RHB-104 was predicted based on PK data obtained from Phase 1 studies and the Phase 3 MAP Study of RHB-104. A Population Pharmacokinetic (popPK) model was individually developed for each component. Following the review of the clinical safety data, and completed HFS Part 1 experiments, the proposed clinical regimen for a FDC product to treat MAC lung disease was developed. Simulations were performed based on the final population PK model for each component (1000 virtual subjects) and summarized for the several dosing regimen combinations. Predicted human exposure for the regimen of clarithromycin 950 mg, rifabutin 240 mg and clofazimine 80 mg daily, in combination and administered in two divided doses three times per week (M-W-F) is presented in Table 5.

TABLE 5

Predicted Steady-State Exposure of Three Antibiotics of a FDC Product of the Present Invention Administered in Combination As the Proposed Clinical Regimen, BID, M-W-F

| | Clarithromycin n = 1000 Dose 475 mg | 14-OH-Clarithromycin n = 1000 | Clofazimine n = 1000 Dose 40 mg | Rifabutin n = 1000 Dose 120 mg | 25-O-Desacetyl Rifabutin n = 1000 |
|---|---|---|---|---|---|
| Week 26 | Arithmetic mean [5$^{th}$-95$^{th}$] | | | | |
| AUC26th, ng · hr/mL | 90600 [32100, 176000] | 83800 [45900, 139000] | 41100 [7410, 102000] | 18800 [10400, 31000] | 2620 [1130, 4900] |
| AUCavg, ng · hr/mL | 12900 [4590, 25100] | 12000 [6560, 19800] | 5870 [1060, 14600] | 2690 [1490, 4430] | 374 [162, 701] |
| Cmax, ng/mL | 1660 [727, 2800] | 1200 [713, 1890] | 301 [73.5, 696] | 248 [149, 387] | 34.4 [14.8, 62.7] |

TABLE 5-continued

Predicted Steady-State Exposure of Three Antibiotics of a FDC Product of the Present Invention Administered in Combination As the Proposed Clinical Regimen, BID, M-W-F

| | Clarithromycin n = 1000 Dose 475 mg | 14-OH-Clarithromycin n = 1000 | Clofazimine n = 1000 Dose 40 mg | Rifabutin n = 1000 Dose 120 mg | 25-O-Desacetyl Rifabutin n = 1000 |
|---|---|---|---|---|---|
| Week 26 | | Arithmetic mean [$5^{th}$-$95^{th}$] | | | |
| AUC26th, ng · hr/mL | 90600 [32100, 176000] | 83800 [45900, 139000] | 41100 [7410, 102000] | 18800 [10400, 31000] | 2620 [1130, 4900] |
| Cmin, ng/mL | 16.4 [6.17e–08, 83.7] | 28.6 [0.0191, 135] | 210 [25.7, 548] | 42.3 [8.12, 97.0] | 5.70 [1.21, 13.7] |
| Cavg, ng/mL | 539 [191, 1050] | 499 [273, 825] | 245 [44.1, 609] | 112 [62.2, 185] | 15.6 [6.74, 29.2] |
| Week 52 | | Arithmetic mean [$5^{th}$-$95^{th}$] | | | |
| AUC52nd, ng · hr/mL | 90600 [32100, 176000] | 84200 [46100, 139000] | 47900 [7410, 131000] | 18900 [10500, 31000] | 2620 [1130, 4900] |
| AUCavg, ng · hr/mL | 12900 [4590, 25100] | 12000 [6590, 19900] | 6850 [1060, 18800] | 2690 [1490, 4430] | 374 [162, 701] |
| Cmax, ng/mL | 1660 [727, 2800] | 1200 [715, 1890] | 342 [73.6, 871] | 248 [149, 387] | 34.4 [14.8, 62.7] |
| Cmin, ng/mL | 16.4 [6.17e–08, 83.7] | 28.9 [0.0199, 136] | 251 [25.8, 731] | 42.4 [8.14, 98.1] | 5.71 [1.21, 13.7] |
| Week 26 | | Arithmetic mean [$5^{th}$-$95^{th}$] | | | |
| AUC26th, ng · hr/mL | 90600 [32100, 176000] | 83800 [45900, 139000] | 41100 [7410, 102000] | 18800 [10400, 31000] | 2620 [1130, 4900] |
| Cavg, ng/mL | 539 [191, 1050] | 501 [275, 829] | 285 [44.1, 783] | 112 [62.3, 185] | 15.6 [6.74, 29.2] |

Abbreviations: AUC26th or AUC52nd = area under the curve on the $26^{th}$ or $52^{nd}$ of twice-daily, three-times-per-week dosing;
AUCavg = daily AUC (weekly AUC/7);
Cmax = maximum concentration;
Cmin = minimum concentration;
Cavg = average concentration over week of dosing;
n = number of subjects;
$5^{th}$-$95^{th}$ = $5^{th}$ and $95^{th}$ percentile.

A target AUC for clarithromycin in ELF was estimated by examining the $5^{th}$ percentile of model-predicted human AUC (see Table 5) under the planned clinical regimen (i.e. 4.59 mg*h/L), and multiplying the range of ELF:total plasma AUC for clarithromycin (i.e. 3.4-7.8). This derivation resulted in a predicted clarithromycin lung exposure, and thus HF exposure, between approximately 15-36 mg*h/L, and thus 20 mg*h/L was selected as the potentially lowest therapeutic exposure, consistent with a 475 mg BID, M-W-F planned clinical clarithromycin dose. A treatment at 50% or 10 mg*h/L was also tested to identify the lowest potential therapeutic exposure for clarithromycin. The following decision was made: the most optimal three drug combination based on the experiments would be that achieving CLR AUC0-24 of approximately 60 mg*h/L, CFZ AUC0-24 of 4.7 mg*h/L, and RFB AUC0-24 of 5.7 mg*h/L. A description of the results of Part 2 is presented herein. The matrix of regimens tested in Part 2 of the study, and resultant AUC0-24 recovered from the system on the final day of sampling, are described in Table 6 and Table 7.

TABLE 6

Additional singlet, doublet, and triplet combination regimens

| | AUCs mg * hr/L | | |
|---|---|---|---|
| Conditions | Clarithromycin dose [AUC] | Clofazimine dose [AUC] | Rifabutin dose [AUC] |
| | NON-TREATED CONTROL | | |
| R1 | — | — | — |
| | SINGLETS | | |
| R2 | 10 | — | — |
| R3 | 20 | — | — |
| R4 | — | 4.7 | — |
| R5 | — | 0.47 | — |
| | DOUBLETS | | |
| R6 | 10 | — | 5.7 |
| R7 | 10 | 4.7 | — |

TABLE 6-continued

Additional singlet, doublet, and triplet combination regimens

| | AUCs mg * hr/L | | |
|---|---|---|---|
| Conditions | Clarithromycin dose [AUC] | Clofazimine dose [AUC] | Rifabutin dose [AUC] |
| R8 | 10 | 0.47 | — |
| R9 | 20 | — | 5.7 |
| R10 | 20 | 4.7 | — |
| R11 | 20 | 0.47 | — |
| TRIPLETS | | | |
| R12 | 18 | 4.7 | 5.7 |
| R13 | 18 | 0.47 | 5.7 |
| R14 | 60 | 7.8 | 5.7 |

TABLE 7

Resultant Hollow Fiber Area Under the Curve for Each Component by-Regimen Tested (Part 2)

| | $AUC_{0-24}$ (mg · h/L) | | |
|---|---|---|---|
| Regimen Code | Clarithromycin | Clofazimine | Rifabutin |
| R1 | — | — | — |
| R2 | 9.44 ± 1.99 | — | — |
| R3 | 18.87 ± 4.63 | — | — |
| R4 | — | 1.24 ± 0.52 | — |
| R5 | — | 0.07 ± 0.01 | — |
| R6 | 9.46 ± 3.13 | — | 7.18 ± 3.86 |
| R7 | 9.70 ± 3.73 | 1.26 ± 0.8 | — |
| R8 | 11.09 ± 3.133 | 0.09 ± 0.04 | — |
| R9 | 19.10 ± 5.91 | — | 8.06 ± 7.02 |
| R10 | 20.41 ± 3.51 | 0.74 ± 0.20 | — |
| R11 | 16.31 ± 4.81 | 0.09 ± 0.06 | — |
| R12 | 15.88 ± 5.11 | 1.24 ± 0.68 | 6.60 ± 6.44 |
| R13 | 18.04 ± 5.43 | 0.06 ± 0.04 | 7.12 ± 6.64 |
| R14 | 62.65 ± 26.24 | 3.07 ± 2.46 | 7.43 ± 6.72 |

Figure 3:
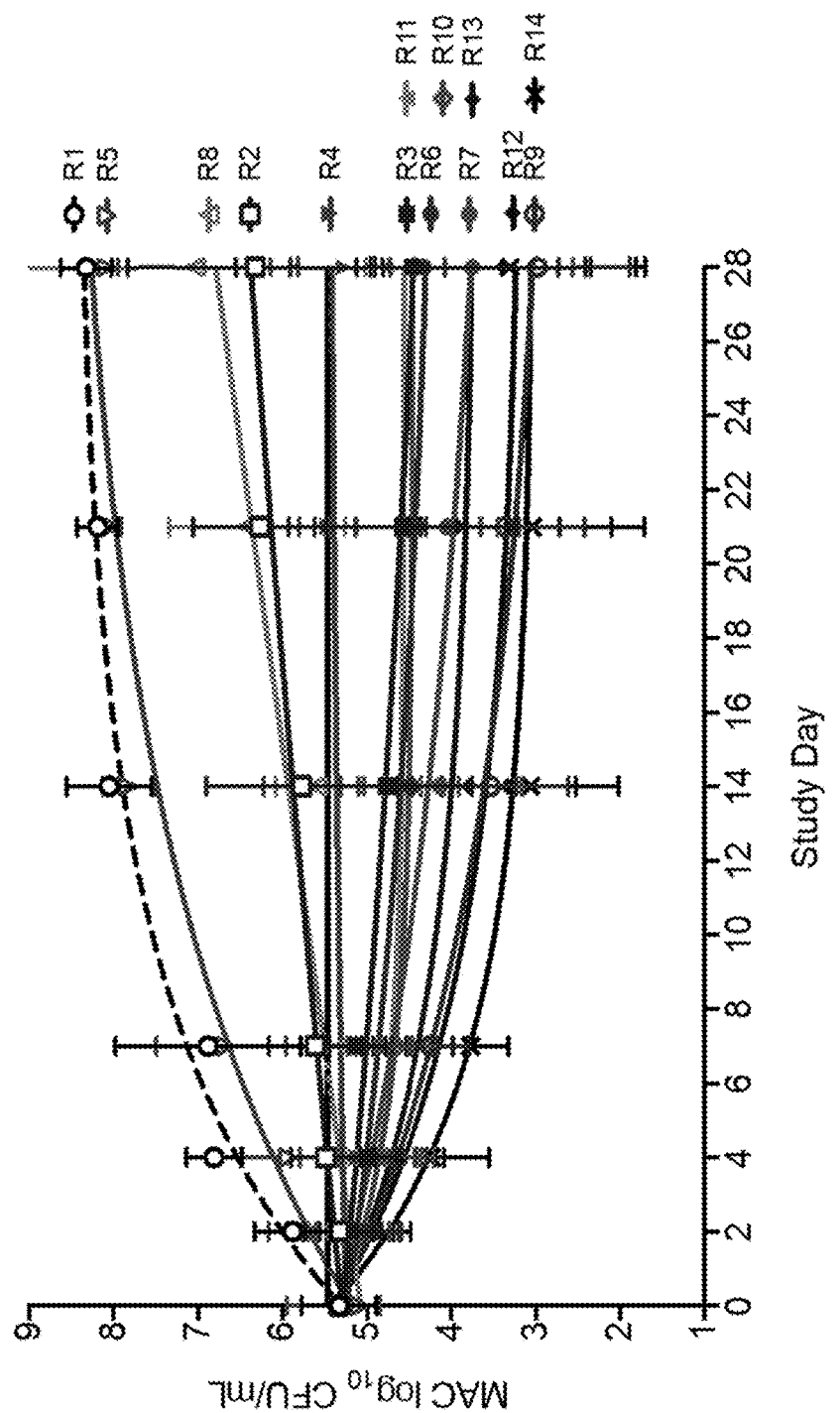
FIG. 3 is a graph of the hollow fiber model fitted microbial kill results by drug regimen tested (monotherapies and combination regimens) based on pharmacokinetics of a fixed dose combination product of the present disclosure.
Figure 4B:
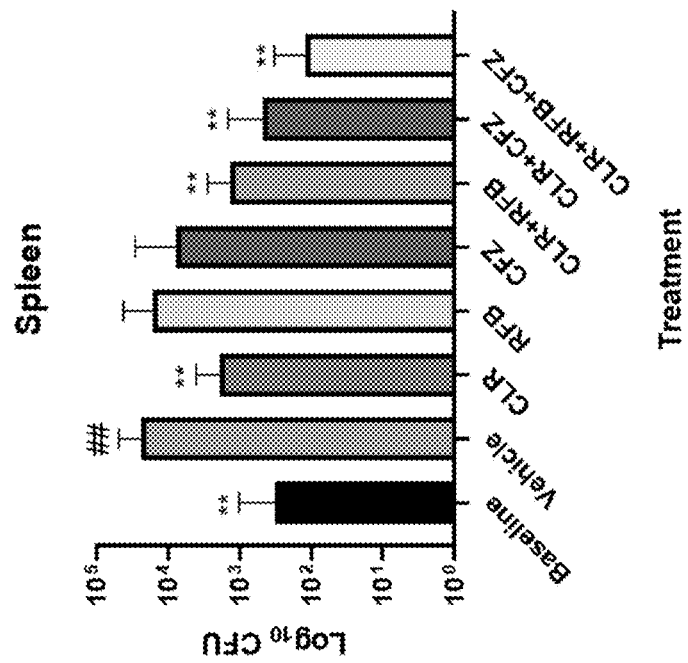
FIG. 4A and FIG. 4B show the mean animal lung CFUs (FIG. 4A) and spleen CFUs (FIG. 4B) by treatment in mice infected with clarithromycin sensitive MAC strain after four weeks of treatment (## $p<0.01$, #### $p<0.0001$ vs. Baseline; * $p<0.05$,  $p<0.01$, ** $p<0.0001$ vs. Vehicle).
Figure 4A:
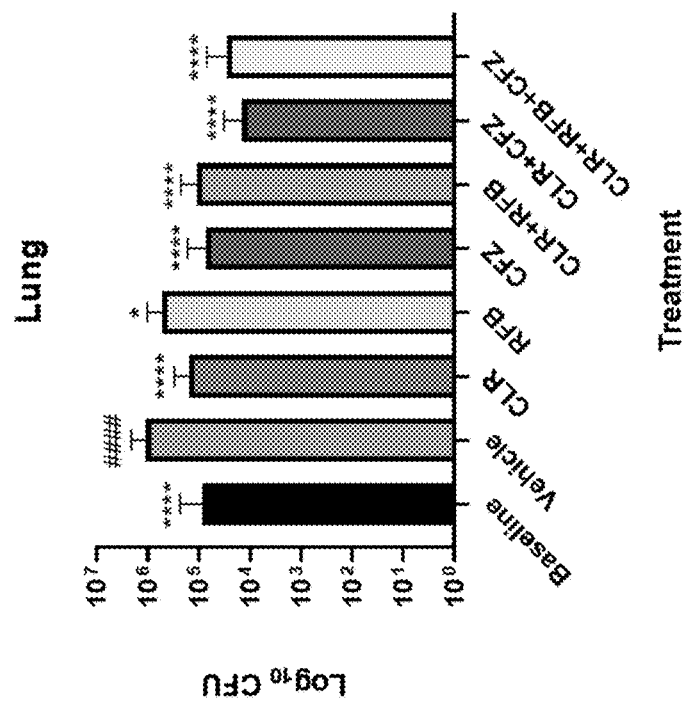
Figure 5B:
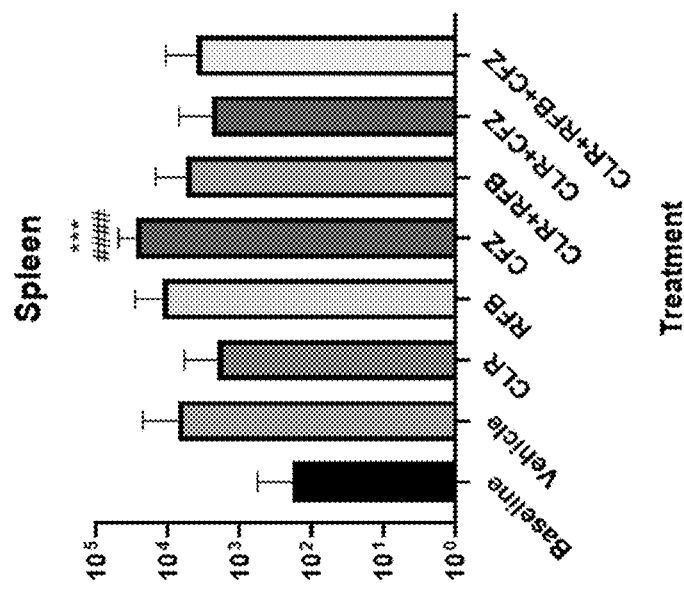
FIG. 5A and FIG. 5B show the mean animal lung CFUs (FIG. 5A) and spleen CFUs (FIG. 5B) by treatment in mice infected with clarithromycin sensitive MAC strain after eight weeks of treatment (## $p<0.01$, #### $p<0.0001$ vs. Baseline; * $p<0.05$,  $p<0.01$, ** $p<0.0001$ vs. Vehicle).
Figure 5A:
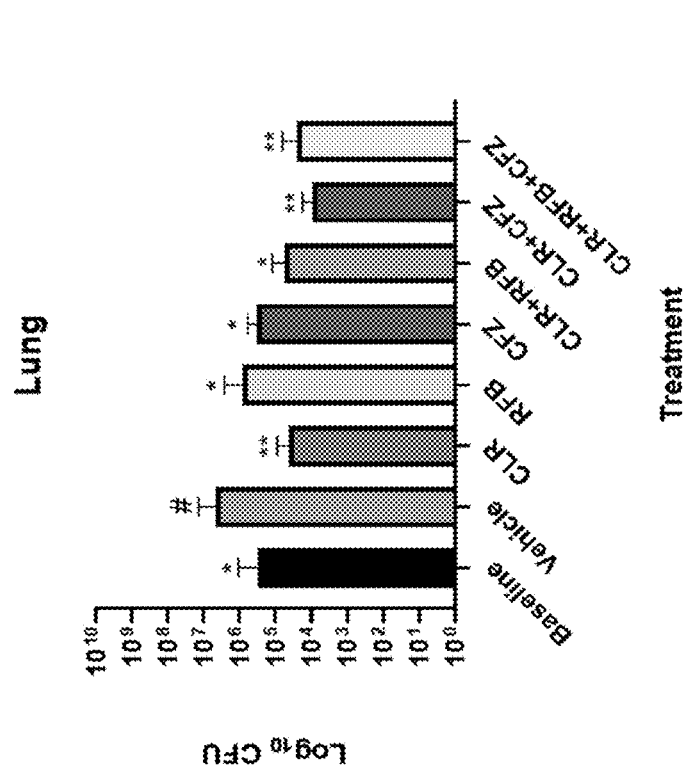
Figures 6A, 6B:
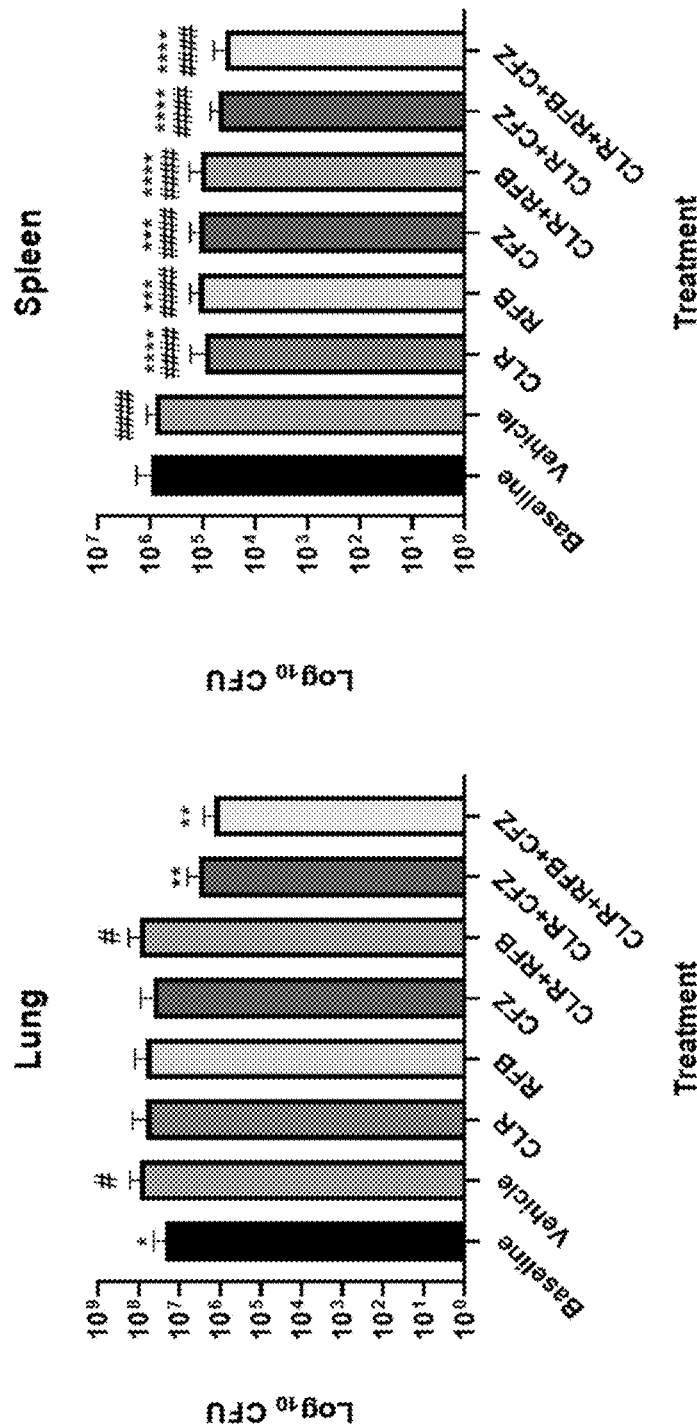
FIG. 6A and FIG. 6B show the mean animal lung CFUs (FIG. 6A) and spleen CFUs (FIG. 6B) by treatment in mice infected with clarithromycin resistant MAC strain after four weeks of treatment (## p<0.01, #### p<0.0001 vs. Baseline; * p<0.05,  p<0.01, ** p<0.0001 vs. Vehicle).
Figures 7A, 7B:
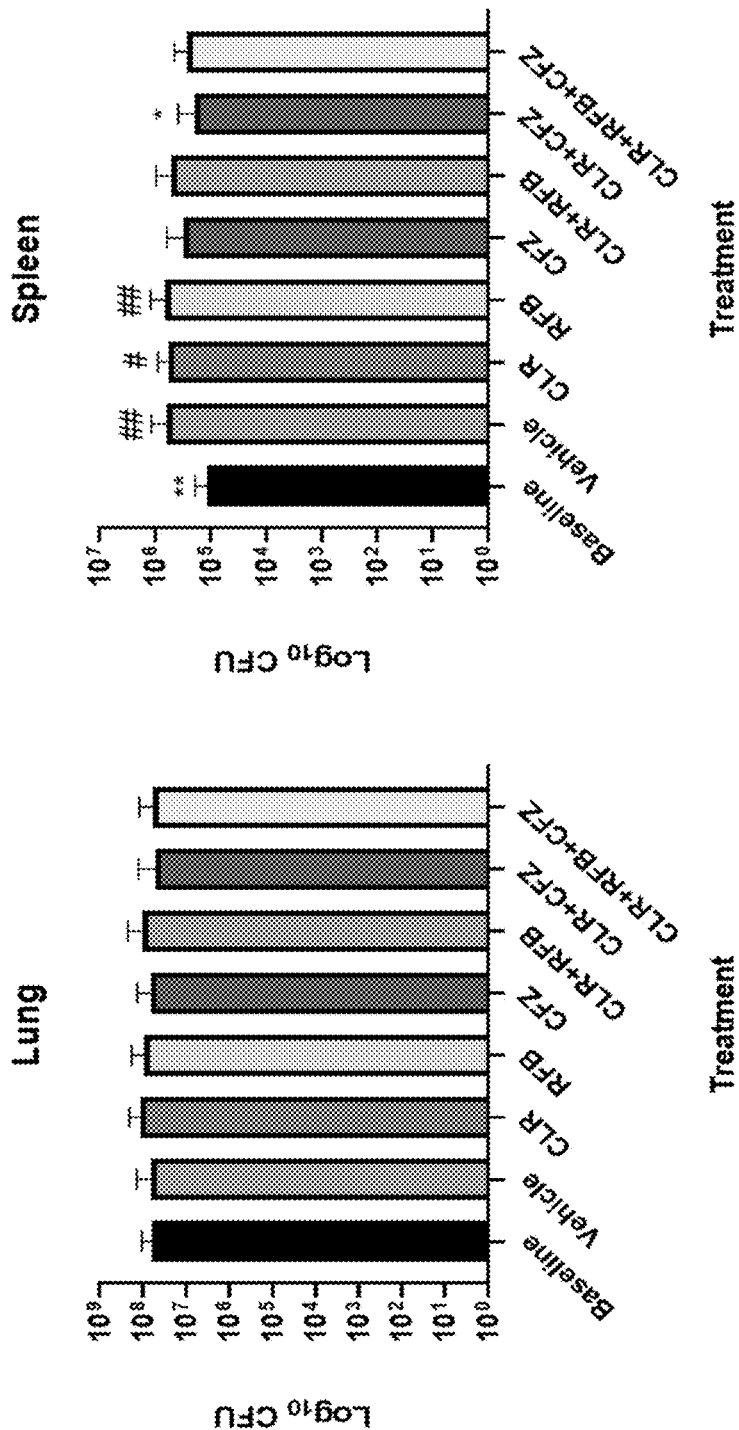
FIG. 7A and FIG. 7B show the mean animal lung CFUs (FIG. 7A) and spleen CFUs (FIG. 7B) by treatment in mice infected with clarithromycin resistant MAC strain after eight weeks of treatment (## p<0.01, #### p<0.0001 vs. Baseline; * p<0.05,  p<0.01, ** p<0.0001 vs. Vehicle).

$AUC_{0-24}$: Area under the concentration vs. time profile over the 24-hour dosing interval at steady-state R14 comprised the exposure for each drug component which resulted in the best kill response from Part 1 as a benchmark for efficacy. FIG. 3 represents the data from five MAC strains [10 replicates] total for monotherapy and different combination therapies, administered daily and Table 8 summarizes the associated kill rate constant and the reciprocal half-life of kill for all tested HF regimens.

The model estimated that the starting bacterial burdens for all regimens, including non-treated controls, were identical. There was no convergence or very poor convergence of the model for the regimens R3, R4, R6; these also had high Akaike Information criteria scores [the lower the score the better]. Since there are no model parameter estimates for R3, R4 and R6, model-fit kill slopes are not presented for these regimens. The kill rate for non-treated control was negative, as was the total kill of −3.1 log 10 CFU/mL, which means the MAC grew, as expected. The same pattern was identified for R2, R5 and R8, while the R7 kill rate had a 95% confidence interval that overlapped with zero. R2, R6 and R7 regimens included a target clarithromycin exposure of 10 mg*h/L, and represent the lowest tested clarithromycin exposure. For the two regimens with low clarithromycin exposure for which kill slopes could be estimated, the HF results demonstrate that clarithromycin doses lower than 475 mg BID, M-W-F are unlikely to yield adequate clinical response. Since clarithromycin is considered the backbone of the regimen, this finding is important in guiding the dose selection for clinical development.

The kill slopes for R9, R11, R12, R13, to R14 had overlapping 95% confidence intervals, and had positive sign indicating kill below day 0 bacterial burden. The maximal kill from R11 and R13 did not have as large a depth of kill as R14, leaving both R9 and R12 performing as well as the best regimen. The R9, while appearing statistically as good as the benchmark regimen in terms of reduction of bacterial burden, exhibited a kill rate constant estimates that was less than 50% that of either R12 or R14, because the kill parameter estimates were imprecise and had high confidence intervals so that the half-life for kill rate for example ranged from 2.84 to ∞ hours. Next, a formal statistical comparison of the model parameters for slope and plateau [maximal kill bacterial burden] of R9, R12, R13, and R14, to test the null hypothesis that the 2 parameters were the same for all data sets; the p-value was 0.03 because of differences in maximal kill which was lower for R13 which had the same kill slope but lower maximal kill burden. A comparison for R12 versus R14 resulted in no significant difference (p=0.355) meaning that R12 and R14 exhibit similar kill slopes and extent of kill as R14 [i.e., regimen with the best possible kill rate], but at lower concentrations. Therefore R12 [CLR AUC0-24 of 16 mg*h/L, CFZ AUC0-24 of 1.2 mg*h/L, and RFB AUC0-24 of 7 mg*h/L], achieved the comparable degree of kill and speed of kill [slope] as the target regimen R14 in which was achieved a CLR AUC0-24 of 63 mg*h/L, a CFZ AUC0-24 of 3 mg*h/L, and a RFB AUC0-24 of 7 mg*h/L] These results support a fairly wide range of clinical viable doses of CLR. The fact that the three-drug combination with lower clofazimine exposure provided for a comparable kill rate constant to the higher clofazimine combination, while resulting in a lower bacterial burden, demonstrated the importance of the three-drug combination and the sensitivity of the results of anti-MAC effect to clofazimine concentration.

TABLE 8

Calculation of mean kill slopes and their 95% confidence intervals by different regimens

| | Initial burden [$\log_{10}$ CFU/mL] | Kill rate constant [$day^{-1}$] | Half Life [Days] | Total kill [$\log_{10}$ CFU/mL] |
|---|---|---|---|---|
| R1 | 5.24 [4.96 to 5.52] | −0.15 [−0.21 to −0.11] | 4.52 [3.35 to 6.44] | −3.13 |
| R2 | 5.24 [4.82 to 5.60] | −0.01 [0 to 0.12] | 56.36 [Wide] | −5.48 |
| R5 | 5.19 [4.73 to 5.63] | −0.09 [0.03 to 0.16] | 7.87 [4.27 to 25.58] | −3.45 |
| R7 | 5.37 [4.93 to 5.86] | 0.18 [0 to 1.16] | 3.75 [0 to ∞] | 0.84 |
| R8 | 4.78 [4.41 to 5.14] | 0.07 [0.05 to 0.10] | 9.49 [6.85 to 13.58] | −2.27 |
| R9 | 5.29 [4.86 to 5.76] | 0.09 [0 to 0.24] | 7.78 [2.84 to ∞] | 1.99 |
| R10 | 5.38 [4.92 to 5.87] | 0.35 [0.06 to ∞] | 1.98 [0-12.15] | 0.72 |
| R11 | 5.35 [4.86 to 5.86] | 0.51 [Imprecise] | 1.35 [Imprecise] | 0.51 |
| R12 | 5.42 [4.93 to 5.93] | 0.21 [0.08 to 0.46] | 3.36 [1.52 to 8.94] | 1.58 |

TABLE 8-continued

Calculation of mean kill slopes and their 95% confidence intervals by different regimens

|     | Initial burden [$\log_{10}$ CFU/mL] | Kill rate constant [$day^{-1}$] | Half Life [Days] | Total kill [$\log_{10}$ CFU/mL] |
| --- | --- | --- | --- | --- |
| R13 | 5.37 [4.77 to 5.99] | 0.27 [Imprecise] | 2.54 [1.38 to 18.26] | 0.98 |
| R14 | 5.46 [4.95 to 5.99] | 0.22 [0.11 to 0.40] | 3.18 [1.75 to 6.24] | 2.14 |

In order to relate the HFS exposure to potentially human efficacious doses, an estimation corresponding human plasma exposure can be made by back-calculating the HFS measured AUC to total human plasma AUC by accounting for the ELF:plasma ratio for each drug component. As described above, the HFS is designed such that the fluid circulating throughout the system is analogous to the extracellular fluid that MAC infected cells might be exposed to in the interstitial fluid or epithelial lining fluid (ELF). ELF is understood to be largely protein free and thus the total ELF exposure can be considered largely unbound drug, available to act on the pharmacologic target.

Consideration of ELF to total serum CLR suggests ratios between 3.4-7.8. At the most effective HFS clarithromycin-based regimens, HFS AUC ranged from approximately 10-20 mg·h/L. Regimens associated with this range of exposure were no worse than much higher HFS AUC at approximately 60 mg·h/L. Model-based simulations of human regimens including a 475 mg BID, M-W-F regimen estimate the geometric mean (5th, 95th percentile) daily exposure of 11.3 [4.59, 25.1] mg·h/L. Considering a conservative 3-fold greater penetration into the ELF, all of which would be considered active, the currently proposed clarithromycin regimen of 475 mg BID, M-W-F, is considered to be adequate to support extrapolation of the clarithromycin results from the HFS experiments. Similar calculations were performed for the rifabutin and clofazimine components of the FDC of the present invention (120 mg BID, M-W-F and 40 mg BID, M-W-F, respectively).

For rifabutin, assumptions were based primarily on data available for rifampin which is estimated to have an ELF:plasma of approximately 0.34, although it is suggested that intracellular penetration is several fold greater for rifabutin compared to rifampin. Model-based simulations of 120 mg BID, M-W-F in humans (administered in combination with clarithromycin and clofazimine) result in a predicted geometric mean ($5^{th}$, $95^{th}$ percentile) daily exposure of 2.54 [1.49, 4.43] mg·h/L. When compared to the rifabutin HFS AUC associated with the best kill (approximately 7 mg·h/L), predicted human exposure is approximately $\frac{1}{10}^{th}$ of the rifabutin exposure associated with the best kill when combined with a clarithromycin-based regimen, however the HFS exposure was associated with a large standard deviation approximately the same magnitude of the mean, suggesting a wide range of rifabutin exposure is effective when combined with a macrolide regimen. Moreover higher rifabutin doses (150-300 mg/day) are reported to be poorly tolerated when administered with clarithromycin for NTM lung infection, suggesting the proposed average daily rifabutin dose (120 mg BID, M-W-F equivalent to approximately 100 mg/day, every day of the week), is likely to be better tolerated than the higher doses historically reported to be used in NTM and related infections.

Estimates of ELF exposure from Dheda et al., Drug-Penetration Gradients Associated with Acquired Drug Resistance in Patients with Tuberculosis. Am J Respir Crit Care Med 2018, 198 (9), 1208-1219, can be drawn from airway concentrations, which for clofazimine, were approximately 0.19% (corresponding to a ratio of 0.0019). Model-based simulations of 40 mg BID, M-W-F in humans (administered in combination with clarithromycin and rifabutin) results in a predicted geometric mean ($5^{th}$, $95^{th}$ percentile) daily exposure of 4.73 [10.6, 18.8]. While the best performing triplet regimen containing clofazimine was associated with a HFS AUC of approximately 1-3 mg·h/L, the triplet regimen with a clofazimine AUC of approximately 0.06±0.04 mg·h/L performed better than clarithromycin monotherapy regimens and doublets with clofazimine and clarithromycin. Given an approximate ELF:plasma ratio of 0.0019, the estimated ELF exposure from a 40 mg BID, M-W-F regimen is anticipated to overlap with the range of exposure associated with reasonable kill rate constants in the HFS experiments.

In summary, the HF experiments demonstrate that of the singlet treatments, only clarithromycin resulted in reductions in colony forming units (CFUs), whereas CFU counts increased with rifabutin or clofazimine alone. Two-drug combinations of clarithromycin and rifabutin or clarithromycin and clofazimine, performed better than clarithromycin alone. This finding supports the importance of a second antibiotic added to a clarithromycin backbone regimen, even when the additional antibiotic does not demonstrate killing efficacy alone. The maximal effect on MAC killing was observed with the triple-drug combination with the depth of kill sensitive to the exposure of clofazimine in the regimen.

These results also support the dose of each FDC component in that the HF responses suggest that response to the macrolide is largely at the maximum response/best depth of kill at systemic exposures anticipated under the planned clinical dose (and treatment guidelines). Although higher exposures of clofazimine and rifabutin may confer some additional in vitro benefit in terms of reduction of MAC burden, the planned clinical doses were selected to balance the benefit risk by reducing the risk of safety events associated with these treatments (e.g. QTc prolongation for clofazimine, and liver function abnormalities, uveitis for rifabutin).

Example 3—to Evaluate the Contribution of CFZ, CLR and RFB, Alone, and in Combination, to the Antibacterial Effect Against *Mycobacterium Avium* Complex (MAC) in an In Vitro Biofilm Model of Infection

*Mycobacterium avium* subsp. *hominissuis* (MAH) (*M. avium* strains 104, A5 [clarithromycin resistant strain in biofilm experiment] and 101 [clarithromycin resistant strain in the in vivo mouse experiments] were isolated from the blood and lung of patients. *M. avium* 104 was obtained from a patient at UCLA, *M. avium* A5 was obtained from a patient in England, and *M. avium* 101-R was obtained from a patient at UCLA. Clarithromycin resistant sub-subpopulation was sequenced and was determined to have a single base mutation in the 23 S RNA gene ($A_{2275}$ to a $C_{2275}$) that confers resistance to clarithromycin (MIC>128 µg/mL).

The bacteria were recovered from storage at −80° C. by culturing on nutrient agar at 37° C. under aerobic conditions. Following visual check to ensure appropriate colony characteristics and purity, the strain was deemed suitable for use. Inoculum stocks of M. avium were prepared for use in infection models by resuspension in Hank's buffered salt solution (HBSS) to desirable concentrations, by comparing with McFarland #1 turbidity standards. Bacteria were passed through a 23-gauge needle ten times to disperse clumps. For in vitro and in vivo experiments, the dispersion of the inoculum was confirmed microscopically. Inoculums were diluted and plated onto 7H10 agar to confirm the concentration of bacteria.

Determination of the MIC of Antibiotics

Susceptibility testing was conducted using broth microdilution single and twofold dilutions as described in the literature. Suspensions were prepared by swabs on a growth plate with a sterile cotton swab, or were prepared in broth culture. The growth was transferred to a 4.5 mL of phosphate buffer solution (PBS) until the turbidity matched the density of a 0.5 McFarland standard. Suspensions were then vigorously mixed on a vortex mixer for 15 to 20 seconds. The final inoculum was prepared to a bacterial density of $10^5$. The tube was inverted 8-10 times to mix the suspension.

Biofilm Methodology

Methods described herein are similar to the ones described by Rose and Bermudez, Identification of Bicarbonate as a Trigger and Genes Involved with Extracellular DNA Export in Mycobacterial Biofilm. ASM Journals, mBio, Vol. 7, No. 6 2016. In brief, biofilm experiments were conducted for both clarithromycin sensitive (M. avium 104) and resistant (M. avium A5) strains. 7H10 agar plate(s) were streaked with low passage M. avium 104 and M. avium A5 allowing for one week of log phase growth. Bacteria were suspended from the plate into a tube containing 16 mL of HBSS, creating a suspension of $10^8$ bacteria. The tubes were then diluted 1:10 and an optical density (O.D.) reading from 0.018 to 0.021(absorbance) was obtained. The contents of the bacterial suspension were then poured into a reservoir and allowed to settle for 5 minutes, at the bottom of the reservoir. Using a multi-channel pipette, 150 µL of bacterial suspension was then transferred into a flat bottom 96-well plate. The plates were placed into a sealable plastic bag (Ziploc) to prevent evaporation and the biofilms were allowed to grow by the incubation of the plates at 25° C. in the dark for one week.

To assess the impact of each drug component, the media was replaced with 150 µL of fresh HBSS containing the desired concentrations of antibiotics (CLR: 1.9-4.3 µg/mL; RFB: 0.04 µg/mL and CFZ: 0.0005 µg/mL). Concentrations for biofilm assessments were determined first by estimating the average concentration at steady-state for each drug component when administered in combination for the treatment of MAC lung infection and multiplying by an estimated epithelial lining fluid (ELF) concentration to total plasma concentration ratio. The penetration of CLR into epithelial lining fluid (ELF) i.e., ELF:plasma ratio, is relatively well documented and has been reported to range from 3.4-7.8. As ELF is largely free of plasma proteins, the free average ELF concentration at the airway-biofilm interface is therefore 3.4-7.8 fold greater than the average total concentration at steady-state in plasma. For RFB, there is little data to inform the ELF:plasma ratio, however ratios of approximately 0.34 have been reported for rifampin. For CFZ there is similarly little experimentally derived data to support the ELF:plasma ratio; however, Dheda et al., Drug-penetration gradients associated with acquired drug resistance in patients with tuberculosis. American Journal of Respiratory and Critical Care Medicine, 198(9): 1208-1219, November 2018, obtained airway and blood concentration data in a limited group of individuals, which resulted in an estimated ELF:plasma ratio of approximately 0.2%.

Antibiotic-treated plates were placed back in the plastic bag and incubated at 25° C. in the dark for either four or seven days. Following the incubation period, the contents of the wells in the plate were disrupted with vigorous pipetting. The suspension was then diluted in HBSS from $10^{-3}$ to $10^{-5}$ and plated onto 7H10 agar plates. Bacteria were allowed to grow for 10 days before determining the surviving colony forming units (CFU)/ml.

Pairwise comparisons were made and determined by the Mann-Whitney non-parametric test (Graphpad Prism version 7).

Effect of Clarithromycin, Rifabutin and Clofazimine on Biofilms

Relative to the initial inoculum of M. avium 104, organisms grew in all treatment samples. After four and seven days of clinically relevant drug exposure, CFU/mL were significantly lower in the three-drug combination compared to individual drug and two-drug combinations suggesting that the combination treatment is superior in anti-MAC activity against organisms which form extracellular biofilm matrices in the airways (Table 9).

TABLE 9

Mean ± SD Colony Forming Unit Concentration After Four and Seven Days of Exposure to CFZ, CLR and RFB Components Alone and In Combination

| Treatment (Drug) | CFU/mL | | Notes |
| --- | --- | --- | --- |
| | Four Days | Seven Days | |
| HBSS | $1.69 \pm 0.4 \times 10^7$ | $5.2 \pm 0.5 \times 10^7$ | |
| Clarithromycin | $1.35 \pm 0.3 \times 10^7$ | $1.07 \pm 0.3 \times 10^7$ | 1 |
| Rifabutin | $1.41 \pm 0.5 \times 10^7$ | $1.64 \pm 0.3 \times 10^7$ | 1 |
| Clofazimine | $1.91 \pm 0.6 \times 10^7$ | $1.42 \pm 0.5 \times 10^7$ | 1 |
| Clarithromycin/Rifabutin | $1.38 \pm 0.3 \times 10^7$ | $7.52 \pm 0.6 \times 10^6$ | 1, 2, 3 |
| Clarithromycin/Clofazimine | $1.33 \pm 0.4 \times 10^7$ | $1.08 \pm 0.5 \times 10^7$ | 1 |
| Clarithromycin/Rifabutin/Clofazimine | $3.00 \pm 0.4 \times 10^6$ | $1.16 \pm 0.5 \times 10^6$ | 1, 2, 3, 4, 5, 6 |

Abbreviation: CFU = colony forming unit;
HBSS = Hanks Balanced Salt Solution;
SD = standard deviation
Note:
1: $p < 0.05$ compared to HBSS control, 2: $p < 0.05$ compared with clarithromycin treatment; 3: p +21 0.05 compared with rifabutin treatment; 4: $p < 0.05$ compared with clofazimine treatment; 5: $p < 0.05$ compared with clarithromycin + rifabutin; 6: $p < 0.05$ compared with clarithromycin + clofazimine

Example 4—CFZ, CLR and RFB Components Exhibit Greater Efficacy in Combination than Alone in Mouse Models of NTM Infection A series of in vivo mouse studies was conducted to further evaluate the contribution of each component in the FDC product of the present invention, and to assess the contribution of each component in suppressing the emergence of macrolide resistant strains. The in vivo lung infection of *M. avium*-infected mice treated with clarithromycin, rifabutin and clofazimine as individual drugs and in combination was examined. In this study, mice were inoculated with pathogen(s) and allowed to develop a NTM lung infection over a three-week period before any treatments were initiated. The specific strain used in this set of experiments was *Mycobacterium avium* subsp. *hominissuis* (MAH) and the treatment effect against both clarithromycin sensitive (*M. avium* strain 104) and clarithromycin resistant strains (*M. avium* strain 101-clari-R) was assessed. Once infection was established, mice were treated orally, once-daily, with single-agent, dual therapy or three-drug combination therapy for up to four or eight weeks after the establishment of infection.

Clarithromycin was dosed at 50 mg/kg, which is the lowest effect mg/kg daily dose in mice previously demonstrated to be effective and predicted to result in comparable systemic exposure to that in humans dosed with 950 mg total daily dose administered in two divided doses, three timed per week (M-W-F). Both rifabutin and clofazimine were dosed at 10 mg/kg/day, which is anticipated to provide for comparable systemic exposure to that in humans when administered at 240 mg and 80 mg total daily doses (in two divided doses), three times per week (M-W-F) for rifabutin and clofazimine, respectively.

Following both the four-week and eight-week treatment period, mice were sacrificed, and lungs and spleens were harvested for CFU counts in each tissue and compared to CFUs recovered in the baseline and vehicle-treated groups. Tissue samples were plated with and without antibiotic on 7H10 agar. Antibiotic plates were made with minimum inhibitory concentrations (MICs) of 8 µg/ml for clarithromycin, and 0.25, µg/ml for both rifabutin (RFB) and clofazimine (CFZ). Plates were made for each of clarithromycin (CLR) alone, clarithromycin plus either rifabutin (CLR+RFB) or clofazimine (CLR+CFZ) and the three-drug combination (CLR+RFB+CFZ). All plates were incubated in a microbiological incubator at 37° C. for 14 days.

A second set of experiments were conducted to assess the contribution of RFB and CFZ in mitigating the selection of resistance when administered a dual agent treatment with CLR or as a three-drug combination treatment. In this experiment, inoculum from harvested lungs were plated on Middlebrook 7H10 agar plates at concentrations other than the MIC of each drug. Homogenates were diluted from $10^{-2}$ to $10^{-6}$ and plated. Observed colonies were tested for MIC. In addition, a range of inoculums of *M. avium* 104 ($10^{11}$ to $10^5$) were incubated with the MIC of the antibiotics in 7H9 broth for seven days and plated onto 7H10 agar plates to determine the frequency of resistance before host infection.

Total bacterial viable counts (CFU/ml of homogenate) were expressed per lung or spleen tissue (CFU/organ). Activity against MAC strains were tabulated and summarized descriptively by treatment group and strain. Descriptive statistics included sample size (N), mean, and standard deviation (SD). Bar plots will be produced to illustrate the side-by-side treatment effects with SD error bars, and stratified by strain. Individual tables and figures will be produced for lung and spleen. Treatment groups were compared using a one-way ANOVA to determine variance between groups. Then treatment groups were independently compared to both baseline and vehicle via a one-way ANOVA at an alpha of 0.05. Tables and plots were produced using R and GraphPad Prism (version 8.0.1) and statistical analysis was performed using GraphPad Prism.

A summary of lung and spleen CFU in mice after four weeks of each treatment is summarized in Table 10 and Table 11, respectively, and in Table 12 and Table 13 after eight weeks of treatment for clarithromycin sensitive strains. Following both the four and eight week treatment period, mice were sacrificed, and lungs and spleens were harvested for CFU counts in each tissue and compared to CFUs recovered in the baseline and vehicle-treated groups. CFU reductions after four and eight weeks of treatment relative to baseline and vehicle treated animals are presented graphically in FIGS. 4A and 4B and FIGS. 5A and 5B for the clarithromycin sensitive, respectively.

In the Tables below: CV=coefficient of variation %; MEAN=mean colony forming units; N=sample size; SD=standard deviation.

TABLE 10

Descriptive Statistics of Lung CFUs in Four-Week CLR Resistant Strain

| GROUP | TREATMENT | N | MEAN | SD | CV |
|---|---|---|---|---|---|
| Baseline | Baseline | 10 | 2.23e+07 | 2.06e+07 | 92.30 |
| A | Vehicle | 10 | 9.48e+07 | 6.85e+07 | 72.27 |
| B | Clarithomycin 50 mg/kg | 10 | 6.53e+07 | 7.6e+07 | 116.45 |
| C | Rifabutin 10 mg/kg | 10 | 6.47e+07 | 5.78e+07 | 89.35 |
| D | Clofazimine 10 mg/kg | 10 | 4.33e+07 | 4.46e+07 | 102.91 |
| E | Clarithromycin 50 mg/kg & Rifabutin 10 mg/kg | 10 | 9.27e+07 | 8.3e+07 | 89.56 |
| F | Clarithromycin 50 mg/kg & Clofazimine 10 mg/kg | 10 | 3.25e+06 | 3.14e+06 | 96.59 |
| G | Clarithromycin 50 mg/kg & Rifabutin 10 mg/kg & Clofazimine 10 mg/kg | 10 | 1.37e+06 | 1.11e+06 | 80.84 |

TABLE 11

Descriptive Statistics of Spleen CFUs in Four-Week CLR Resistant Strain

| GROUP | TREATMENT | N | MEAN | SD | CV |
|---|---|---|---|---|---|
| Baseline | Baseline | 10 | 9.65e+05 | 8.53e+05 | 88.35 |
| A | Vehicle | 10 | 8.06e+05 | 3.5e+05 | 43.42 |
| B | Clarithomycin 50 mg/kg | 10 | 8.89e+04 | 7.98e+04 | 89.78 |
| C | Rifabutin 10 mg/kg | 10 | 1.19e+05 | 5.46e+04 | 45.92 |
| D | Clofazimine 10 mg/kg | 10 | 1.15e+05 | 5.94e+04 | 51.57 |
| E | Clarithromycin 50 mg/kg & Rifabutin 10 mg/kg | 10 | 1.08e+05 | 7.01e+04 | 64.66 |
| F | Clarithromycin 50 mg/kg & Clofazimine 10 mg/kg | 10 | 4.98e+04 | 2.1e+04 | 42.20 |
| G | Clarithromycin 50 mg/kg & Rifabutin 10 mg/kg & Clofazimine 10 mg/kg | 10 | 3.68e+04 | 2.47e+04 | 67.24 |

TABLE 12

Descriptive Statistics of Lung CFUs in Eight-Week CLR Resistant Strain

| GROUP | TREATMENT | N | MEAN | SD | CV |
|---|---|---|---|---|---|
| Baseline | Baseline | 12 | 6.01e+07 | 4.62e+07 | 76.92 |
| A | Vehicle | 12 | 6.49e+07 | 7.34e+07 | 113.21 |
| B | Clarithomycin 50 mg/kg | 12 | 1.14e+08 | 9.17e+07 | 80.63 |
| C | Rifabutin 10 mg/kg | 12 | 9.38e+07 | 8.83e+07 | 94.12 |
| D | Clofazimine 10 mg/kg | 12 | 6.61e+07 | 6.73e+07 | 101.88 |
| E | Clarithomycin 50 mg/kg & Rifabutin 10 mg/kg | 12 | 1.03e+08 | 1.18e+08 | 114.73 |
| F | Clarithromycin 50 mg/kg & Clofazimine10 mg/kg | 12 | 5.16e+07 | 7.56e+07 | 146.48 |
| G | Clarithromycin 50 mg/kg & Rifabutin 10 mg/kg & Clofazimine 10 mg/kg | 12 | 5.840+07 | 6.21e+07 | 106.28 |

TABLE 13

Descriptive Statistics of Spleen CFUs in Eight-Week CLR Resistant Strain

| GROUP | TREATMENT | N | MEAN | SD | CV |
|---|---|---|---|---|---|
| Baseline | Baseline | 12 | 1.16e+05 | 7.58e+04 | 65.35 |
| 1 | Vehicle | 12 | 6.1e+05 | 5.57e+05 | 91.34 |
| B | Clarithomycin 50 mg/kg | 12 | 5.8e+05 | 3.21e+05 | 55.27 |
| C | Rifabutin 10 mg/kg | 12 | 6.67e+05 | 5.34e+05 | 80.00 |
| D | Clofazimine 10 mg/kg | 12 | 3.09e+05 | 3.07e+05 | 99.39 |
| E | Clarithomycin 50 mg/kg & Rifabutin 10 mg/kg | 12 | 5.1e+05 | 4.49e+05 | 88.03 |
| F | Clarithromycin 50 mg/kg & Clofazimine 10 mg/kg | 12 | 1.95e+05 | 1.88e+05 | 96.00 |
| G | Clarithromycin 50 mg/kg & Rifabutin 10 mg/kg & Clofazimine 10 mg/kg | 12 | 2.67e+05 | 1.87e+05 | 70.03 |

TABLE 14

Descriptive Statistics of Lung CFUs in Four-Week CLR Resistant Strain

| GROUP | TREATMENT | N | MEAN | SD | CV |
|---|---|---|---|---|---|
| Baseline | Baseline | 10 | 2.23e+07 | 2.06e+07 | 92.30 |
| A | Vehicle | 10 | 9.48e+07 | 6.85e+07 | 72.27 |
| B | Clarithomycin 50 mg/kg | 10 | 6.53e+07 | 7.6e+07 | 116.45 |
| C | Rifabutin 10 mg/kg | 10 | 6.47e+07 | 5.78e+07 | 89.35 |
| D | Clofazimine 10 mg/kg | 10 | 4.33e+07 | 4.46e+07 | 102.91 |
| E | Clarithornycin 50 mg/kg & Rifabutin 10 mg/kg | 10 | 9.27e+07 | 8.3e+07 | 89.56 |
| F | Clarithromycin 50 mg/kg & Clofazimine 10 mg/kg | 10 | 3.25e+06 | 3.14e+06 | 96.59 |
| G | Clatithromycin 50 mg/kg & Rifabutin 10 mg/kg & Clofazimine 10 mg/kg | 10 | 1.37e+06 | 1.11e+06 | 80.84 |

TABLE 15

Descriptive Statistics of Spleen CFUs in Four-Week CLR Resistant Strain

| GROUP | TREATMENT | N | MEAN | SD | CV |
|---|---|---|---|---|---|
| Baseline | Baseline | 10 | 9.65e+05 | 8.53e+05 | 88.35 |
| A | Vehicle | 10 | 8.06e+05 | 3.5e+05 | 43.42 |
| B | Clarithomycin 50mg/kg | 10 | 8.89e+04 | 7.98e+04 | 89.78 |
| C | Rifabutin 10 mg/kg | 10 | 1.19e+05 | 5.46e+04 | 45.92 |
| D | Clofazimine 10 mg/kg | 10 | 1.15e+05 | 5.94e+04 | 51.57 |
| E | Clarithomycin 50mg/kg & Rifabutin 10 mg/kg | 10 | 1.08e+05 | 7.01e+04 | 64.66 |
| F | Clarithromycin 50 mg/kg & Clofazimine 10 mg/kg | 10 | 4.98e+04 | 2.1e+04 | 42.20 |
| G | Clarithromycin 50 mg/kg & Rifabutin 10 mg/kg & Clofazimine 10 mg/kg | 10 | 3.68e+04 | 2.47e+04 | 67.24 |

TABLE 16

Descriptive Statistics of Lung CFUs in Eight-Week CLR Resistant Strain

| GROUP | TREATMENT | N | MEAN | SD | CV |
|---|---|---|---|---|---|
| Baseline | Baseline | 12 | 6.01e+07 | 4.62e+07 | 76.92 |
| A | Vehicle | 12 | 6.49e+07 | 7.34e+07 | 113.21 |
| B | Clarithomycin 50 mg/kg | 12 | 1.14e+08 | 9.17e+07 | 80.63 |
| C | Rifabutin 10 mg/kg | 12 | 9.38e+07 | 8.83e+07 | 94.12 |
| D | Clofazimine 10 mg/kg | 12 | 6.61e+07 | 6.73e+07 | 101.88 |
| E | Ciarithornycin 50 mg/kg & Rifabutin 10 mg/kg | 12 | 1.03e+08 | 1.18e+08 | 114.73 |
| F | Clarithromycin 50 mg/kg & Clofazimine 10 mg/kg | 12 | 5.16e+07 | 7.56e+07 | 146.48 |
| G | Clarithromycin 50 mg/kg & Rifabutin 10 mg/kg & Clofazimine 10 mg/kg | 12 | 5.84e+07 | 6.21e+07 | 106.28 |

In both the four and eight week experiments, baseline group animals demonstrated that the infection took root in the majority of inoculated animals with both lung and spleen exhibiting high bacteria burden. Vehicle treated animals exhibited increased CFUs indicating that the infection continued to fester in untreated animals. Relative to vehicle, clarithromycin alone resulted in an approximately 1- and 2-log unit reduction in CFU after four and eight weeks of treatment, respectively. The mean response of the three-drug combination was similar to the clofazimine-clarithromycin combination in lung tissue; however, the distribution of individual animal data supports a stronger response to the three-drug combination than any two-drug combination.

Results in splenic tissue followed similar trends as in lung, with respect to treatment effects. Although the baseline CFU counts were on average 3 log units lower in the spleen three weeks following lung inoculation.

A summary of lung and spleen CFU in mice after four weeks of each treatment is summarized in Table 14 and Table 15, respectively, and in Table 16 and Table 17 after eight weeks of treatment for clarithromycin sensitive strains. Following both the four and eight week treatment period, mice were sacrificed, and lungs and spleens were harvested for CFU counts in each tissue and compared to CFUs recovered in the baseline and vehicle-treated groups. CFU reductions after four and eight weeks of treatment relative to baseline and vehicle treated animals are presented graphically in FIGS. 6A and 6B and FIGS. 7A and 7B for the clarithromycin sensitive, respectively.

TABLE 17

Descriptive Statistics of Spleen CFUs in Eight-Week CLR Resistant Strain

| GROUP | TREATMENT | N | MEAN | SD | CV |
|---|---|---|---|---|---|
| Baseline | Baseline | 12 | 1.16e+05 | 7.58e+04 | 65.35 |
| A | Vehicle | 12 | 6.1e+05 | 5.57e+05 | 91.34 |
| B | Clarithomycin 50 mg/kg | 12 | 5.8e+05 | 3.21e+05 | 55.27 |
| C | Rifabutin 10 mg/kg | 12 | 6.67e+05 | 5.34e+05 | 80.00 |
| D | Clofazimine 10 mg/kg | 12 | 3.09e+05 | 3.07e+05 | 99.39 |
| E | Clarithromycin 50 mg/kg Rifabutin 10 mg/kg | 12 | 5.1e+05 | 4.49e+05 | 88.03 |
| F | Clarithromycin 50 mg/kg & Clofazimine 10 mg/kg | 12 | 1.95e+05 | 1.88e+05 | 96.00 |

TABLE 16

Descriptive Statistics of Lung CFUs in Eight-Week CLR Resistant Strain

| GROUP | TREATMENT | N | MEAN | SD | CV |
|---|---|---|---|---|---|
| G | Clarithromycin 50 mg/kg & Rifabutin 10 mg/kg & Clofazimine 10 mg/kg | 12 | 2.67e+05 | 1.87e+05 | 70.03 |

Baseline group animals demonstrate that the infection took root in the majority of animals inoculated with both lung and spleen exhibiting high bacteria burden. Vehicle treated animals exhibited increased CFU indicating that the infection continued to fester in untreated animals. In the clarithromycin sensitive infection groups, treatment with individual components exhibited mean reductions in CFUs in both lung and splenic tissues, with both two-drug combinations performing, on average, better than their respective mono-therapy comparators. The mean effect of the three-drug combination was similar to the clofazimine-clarithromycin combination in lung tissue however the distribution of individual animal data supports a stronger response to the three-drug combination than any two-drug combination. Moreover, in splenic tissues, the CFU response was greatest in the three-drug combination.

When administered to mice infected with a clarithromycin resistant strain, individual components were largely ineffective on their own in terms of lung CFU counts, with all single-drug treatments resulting in increased infection burden. In stark contrast, the combination of clofazimine and clarithromycin resulted in reductions in lung CFUs, with an even greater average effect with the three-drug combination, where the bacteria load fell below that at baseline. These results suggest that addition of clofazimine and both clofazimine and rifabutin are increasingly synergistic to the effects of clarithromycin, and appear to counteract clarithromycin resistance mechanisms, suggesting that the three-drug combination may be effective even in a setting of clarithromycin resistance.

In the clarithromycin sensitive experiments, one animal in the clarithromycin monotherapy treatment was identified as having 200 CFUs resistant to clarithromycin. When this bacteria was plated out with agar containing rifabutin and clarithromycin, the number of resistant CFUs reduced by half to 100 CFUs. Additionally, none of the CFUs were found to be resistant to clofazimine and rifabutin nor the three-drug combination. Out of 20 mice receiving the combination of clarithromycin and rifabutin or clarithromycin and clofazimine none had any resistant CFU.

These results provide further support with respect to the contribution of each individual component in terms of activity when treating MAC-lung infections and support the superiority of the three-drug combination over individual component and/or two-drug combinations with a clarithromycin backbone.

Lung and Spleen Histopathology of Mice Infected with MAC and Treated with FDC Components Alone and in Combination for Four and Eight Weeks of Treatment Each of the experimental group had eight cut examined from each lung (8×2 lungs=16×2 mice=32 sections). Lungs were normal and not showing any pathology at pre-infection. Table 18 shows the histopathology findings in the lung in each of the treatment groups.

TABLE 1

Lung Histopathology Findings

| Treatment | Lung Histopathology Findings |
|---|---|
| Saline | Marked multifocal lymphocytic and plasma cell infiltration, diffuse congestion |
| | Dense infiltrates of lymphocytes, plasma cells, and macrophages, infiltrate of the blood vessels, forming nodes or granulomas with many bacteria |
| | Bacteria in the tissue, nodes and mucosal area |
| Clarithromycin | Moderate multifocal lymphocytic and plasma cell in the adventitia of multifocal pulmonary blood vessels, forming nodular aggregates or granulomas with bacteria |
| | Perivascular inflammation, with minimal peribronchiolar lymphocytic infiltration |
| | Diffuse congestion; bacteria in granulomas |
| Rifabutin | Diffuse congestion |
| | Moderate and sometimes marked infiltration of lymphocytes and plasma cells in the adventitia of multiple pulmonary blood vessels, forming granulomas and aggregates, bacteria |
| | Infiltrates of lymphocytes are also observed in multiple locations in the bronchi and bronchioles |
| Clofazimine | Mild diffuse congestion |
| | Minimal multi-focus congestion of lymphocytes and plasma cells |
| | Granulomas in multiple locations with mild number of bacteria |
| | Infiltrates into the bronchiolar walls |
| Clarithromycin & Clofazimine | Multi-diffuse congestion |
| | Minimal multifocal infiltrates of lymphocytes and plasma cells in the lung tissue and in the bronchiole walls |
| | Limited number of granulomas with few bacteria |

TABLE 1-continued

Lung Histopathology Findings

| Treatment | Lung Histopathology Findings |
|---|---|
| Clarithromycin & Rifabutin | Mild to moderate and sometimes marked infiltration of the adventitia of multiple pulmonary blood vessels with lymphocytes and plasma cells, forming nodular aggregates with bacteria<br>Infiltrate in the walls of the airways |
| Clarithromycin & Rifabutin & Clofazimine | Minimal diffuse congestion<br>Minimal multi-focal infiltrates of lymphocytes, with occasional plasma cells in the bronchial walls<br>Rare resolving granulomas |

Treatment with the three compounds is associated with significant improvement of the pathology in the lung.

Pharmacokinetics of FDC Components Alone and in Combination in Mice Treated Once-Daily for Four and Eight Weeks In total, for each treatment, 12 mice were to be sampled. For the 4 week treatment groups, the 12 mice originated from those in both the CFU (10 mice) and histopathology (2 mice) subgroups. Mice in each group were prospectively assigned to a time point for blood sampling for PK purposes (Table 19).

TABLE 19

Pharmacokinetic Sampling Schedule at Week 4 and Week 8

| Mouse No. | Time From Last Dose (hour) | | | | | |
|---|---|---|---|---|---|---|
| | 0* | 1 | 4 | 8 | 12 | 24 |
| 1 | X | | | | | |
| 2 | X | | | | | |
| 3 | | X | | | | |
| 4 | | X | | | | |
| 5 | | | X | | | |
| 6 | | | X | | | |
| 7 | | | | X | | |
| 8 | | | | X | | |
| 9 | | | | | X | |
| 10 | | | | | X | |
| 11 | | | | | | X |
| 12 | | | | | | X |

*Time 0 sample drawn immediately prior to the last dose.
Abbreviation: No. = number PK analysis was performed for the clarithromycin sensitive experiments only.

Pharmacokinetic parameters of area under the curve over the dosing interval ($AUC_{TAU}$), maximum concentration and steady-state average concentration confirm drug exposure in all treatment groups consistent with the intended drug combinations. In general, exposure of the individual drugs was highest in the four-week study, when compared to the two eight-week studies. This may reflect complex pharmacokinetic properties of the drug combination in mice which have not been previously documented or reflect the small sample size (N=2 mice per time point) used in the PK calculations. In general, steady-state PK parameters for all drug components were quite variable, but provide for comparable average steady-state concentrations which overlap with the range of predicted exposure in humans for a twice a day, three-times-a-week regimen with the proposed clinical doses for the FDC of the present disclosure.

Example 5—Non-Clinical (Mice) Pharmacokinetics and Safety of Three Antibiotics of a FDC Product of the Present Invention Given in Combination and Relationship to Human Pharmacokinetics The pharmacokinetics (PK) of a FDC of the present invention are complex and the resultant exposure of each antibiotic component cannot be inferred based on the exposure of the individual components alone. The PK of CLR and RFB administered alone and in combination in clinical stable patients infected with HIV has been previously reported by Hafner et. al. (1998), however the resultant exposure cannot be readily extrapolated to lower or higher doses than what was studied as the P450 CYP3A4 (CYP3A4) induction by RFB or inhibition by CLR may be influenced by the mg doses and/or ratio of doses of each component. Thus, the proposed FDC of the present invention administered in the proposed BID, M-W-F regimen represents a unique drug combination.

As the proposed clinical regimen is administered BID, M-W-F, an average daily area under the curve (AUCavg) and average concentration at steady-state (Cavg) can be used for comparison purposes and translation of exposure across animal model and human species.

The exposure of each component was also estimated in mice, administered each drug alone and in combination at doses comparable to those intended for testing in mouse disease model studies. The pharmacokinetic (PK) and tolerability of the individual components and combination of components was evaluated in a 7-day mouse tolerability and PK study, the results of which are summarized in brief herein. Sixty (60) female mice were tested, 12 per treatment groups:

Group 1: vehicle control;
Group 2: rifabutin 20 mg/kg
Group 3: rifabutin 60 mg/kg
Group 4: clofazimine 10 mg/kg
Group 5: clofazimine 30 mg/kg
Group 6: clarithromycin 100 mg/kg
Group 7: clarithromycin 200 mg/kg
Group 8: combination of clarithromycin 200 mg/kg, rifabutin 60 mg/kg and clofazimine 30 mg/kg.

There were no safety issues observed related to test-items, including no changes in body weight or clinical signs. Orange urine was observed in 4 mice in the combination group on the last day of testing, consistent with chromaturia known to occur following the administration of rifabutin and clofazimine. Events in 2 animals were observed following blood collection for toxicokinetic analysis, including death in one animal and tremors, hunched posture, piloerection, partly closed eyes and decreased activity in the other. These events were considered secondary to blood collection and not to test-item. Tables 20-22 summarize the observed systemic exposure of antibiotic components administered alone and in combination, once-daily for seven days to mice. AUCtlast: Area under the concentration vs. time profile to the last measurable time point; $C_{avg}$: Average concentration at steady-state defined as AUCtlast/dosing interval (i.e. 24 hours); $C_{max}$: Maximum concentration; $t_{max}$: Time to maximum concentration

TABLE 20

Mean Clarithromycin Pharmacokinetic Parameters in Female C57BL/6 Mouse Plasma Following Oral Administration of Clarithromycin Alone or in Combination with 60 mg/kg Rifabutin and 30 mg/kg Clofazimine on Days 1 and 7

| Row | Day | CLR Dose (mg/kg) | Combination With . . . | $t_{max}$ (hr) | $C_{max}$ (ng/mL) | $AUC_{tlast}$ (hr*ng/ mL) | $C_{avg}$ (ng/mL) |
|---|---|---|---|---|---|---|---|
| 1 | 1 | 100 | | 1 | 3400 | 11100 | — |
| 2 | | 200 | | 1 | 9110 | 36200 | — |
| 3 | | 200 | RFB 60 mg/kg CFZ 30 mg/kg | 1 | 8370 | 44200 | — |
| 4 | 7 | 100 | | 1 | 6130 | 17500 | 729 |
| 5 | | 200 | | 1 | 7430 | 34200 | 1,425 |
| 6 | | 200 | RFB 60 mg/kg CFZ 30 mg/kg | 1 | 10100 | 64900 | 2,704 |

For clarithromycin, given the half-life of the drug, Day 7 exposure is expected to reflect the approximate steady-state exposure in the absence of rifabutin (a known inducer of clarithromycin metabolism). While the time to steady-state of clarithromycin in the presence of rifabutin cannot be verified, the comparison of Groups 7 to 8 (rows 5 vs. 6) suggests that induction of clarithromycin metabolism was not occurring. In fact, higher exposure of clarithromycin with rifabutin and clofazimine, compared to clarithromycin alone, suggest more complex pharmacokinetics than initially anticipated. Nonetheless, based on the Day 7 average concentration, a clarithromycin dose of approximately 50 mg/kg/day to 100 mg/kg/day in mice produces similar systemic exposure to that predicted in humans for a disclosed regimen where 950 mg of clarithromycin is administered in two divided doses, M-W-F.

TABLE 21

Mean Rifabutin Pharmacokinetic Parameters in Female C57BL/6 Mouse Plasma Following Oral Administration of Rifabutin Alone or in Combination with 30 mg/kg Clofazimine and 200 mg/kg Clarithromycin on Days 1 and 7

| Row | Day | RFB Dose (mg/kg) | Combination With . . . | $t_{max}$ (hr) | $C_{max}$ (ng/mL) | $AUC_{tlast}$ (hr*ng/ mL) | Cavg (ng/mL) |
|---|---|---|---|---|---|---|---|
| 1 | 1 | 20 | | 1 | 2310 | 22100 | — |
| 2 | | 60 | | 1 | 5650 | 60200 | — |
| 3 | | 60 | CLR 200 mg/kg CFZ 30 mg/kg | 1 | 5300 | 60400 | — |
| 4 | 7 | 20 | | 1 | 3140 | 26800 | 1,117 |
| 5 | | 60 | | 1 | 5760 | 61400 | 2,558 |
| 6 | | 60 | CLR 200 mg/kg CFZ 30 mg/kg | 1 | 5720 | 109000 | 4,541 |

For rifabutin, Day 7 PK in mice may not be reflective of true steady-state, whether with or without coadminsitration of clarithromycin (a known inhibitor of rifabutin metabolism). Thus direct extrapolation of mouse efficacy data to humans is hampered by the magnitude of the interaction with clarithromycin. Based on approximately proportional pharmacokinetics, the planned clinical dose of rifabutin (i.e., 120 mg BID, M-W-F) is predicted to result in an average concentration at steady-state (95% percentiles) of 112 [62.2, 185] ng/mL at 20-60 mg/kg/day with or without clarithromycin. A 10 mg/kg/day of rifabutin was selected for the nonclinical lung infection models in mice, largely informed

TABLE 22

Mean Clofazimine Pharmacokinetic Parameters in Female C57BL/6 Mouse Plasma Following Oral Administration of Clofazimine Alone or in Combination with 60 mg/kg Rifabutin and 200 mg/kg Clarithromycin on Days 1 and 7

| Row | Day | CFZ Dose (mg/kg) | Combination With . . . | $t_{max}$ (hr) | $C_{max}$ (ng/mL) | $AUC_{tlast}$ (hr*ng/ mL) | Cavg (ng/mL) |
|---|---|---|---|---|---|---|---|
| 1 | 1 | 10 | | 4 | 108 | 2150 | — |
| 2 | | 30 | | 24 | 181 | 3690 | — |
| 3 | | 30 | CLR 200 mg/kg RFB 60 mg · kg | 24 | 152 | 2230 | — |
| 4 | 7 | 10 | | 4 | 277 | 5340 | 223 |
| 5 | | 30 | | 24 | 460 | 9870 | 411 |
| 6 | | 30 | CLR 200 mg/kg RFB 60 mg · kg | 1 | 957 | 19900 | 829 |

As clofazimine has a long half-life (in human in excess of 100 days), accumulation in mice is likely to occur very slowly and Day 7 exposure and may not be fully reflective of that observed after 4 weeks of treatment. Nonetheless, the average concentration after one week in mice receiving 10 mg/kg/day is comparable to that predicted for humans receiving 80 mg daily in two divided doses, M-W-F for approximately one year, supporting the translation of efficacy observed in mouse models of disease, to humans. Moreover, higher doses of clofazimine are predicted to prolong the QTc interval >20 ms and thus pose a risk of ventricular arrhythmias that might otherwise be avoided by administering lower doses of clofazimine and leveraging the intracellular accumulation potential with long-term dosing.

Example 6—Cardiac Safety Requires Consideration of Clofazimine Dosing

To enable the identification of a safe clofazimine dose, evaluation of the cardiac safety data from the RHB-104 formulation was performed. In the MAP Study, patients with Crohn's disease, who were treated with twice daily RHB-104 were assessed for cardiac safety disease study with 12-lead ECGs and continuous rhythm recording for 5 minutes at 8 time points over 52 weeks of treatment, and read by a central ECG laboratory.

A concentration vs. QTcF analysis was performed on a subset of data from the MAP Study where the PK sample was drawn within 1 hour of ECG extraction. The rationale for this window was based primarily on the assumption that at least for the rifabutin and clofazimine components, the long half-life would result in modest fluctuation of concentration over the dosing interval and thus the concentrations used in the analysis would enable fitting of a linear model suitable for prediction of the effect at the maximum concentration for each component ($C_{max}$). Initially, a full model (including clarithromycin, 14-OH-clarithromycin, rifabutin, 25-O-desacetyl-rifabutin, and clofazimine) with random intercept and slopes per subject was fit and an unstructured covariance structure was used. This model did not converge. Several models were then assessed with the best model retained, where only clofazimine concentration was retained as the drug component predictor of QT response.

Figure 8:
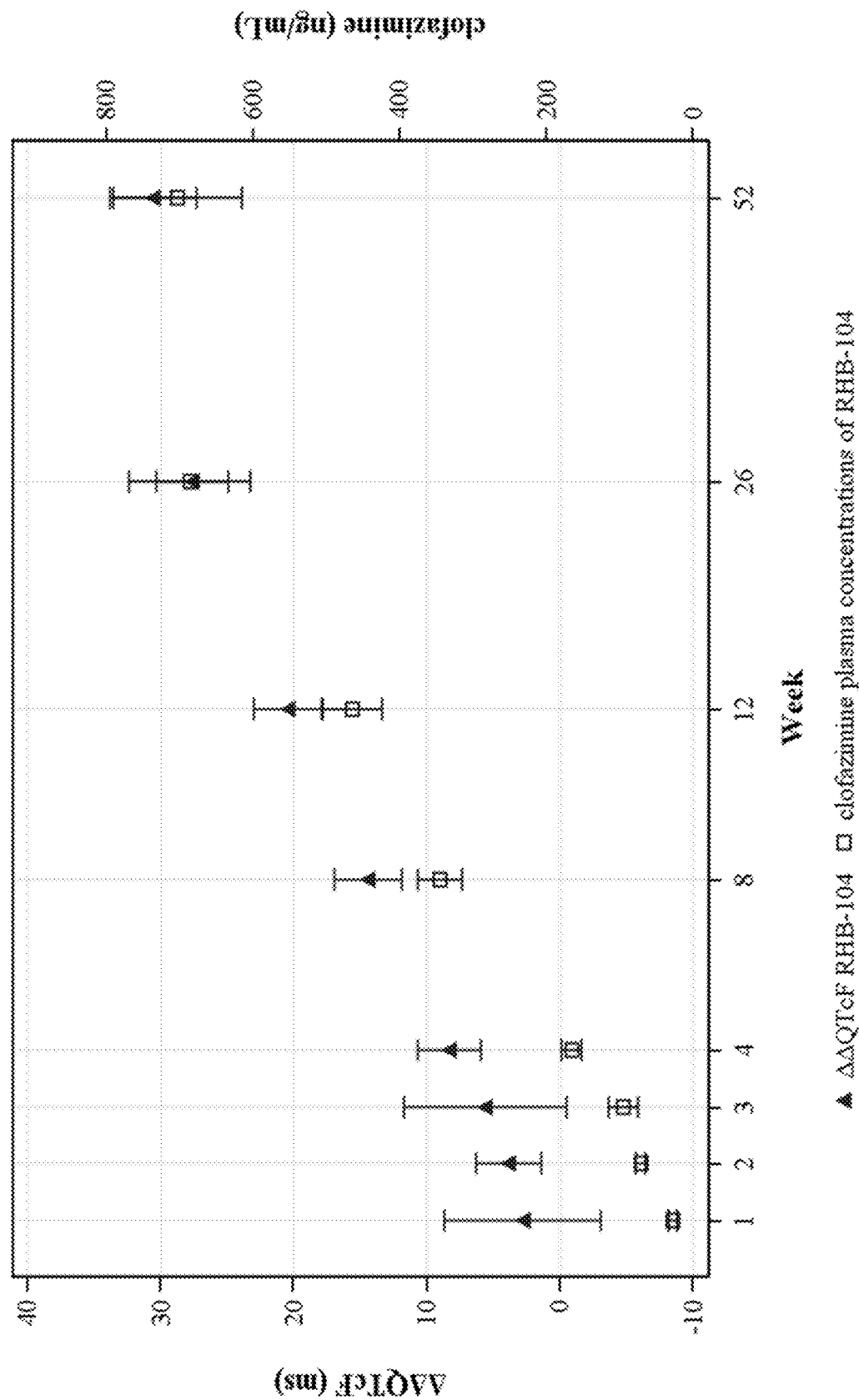
FIG. 8 is a joint plot of clofazimine plasma concentrations and ΔΔQTcF over time for RHB-104 (QT/QTc analysis set, PK/QTc analysis set). Error bars for ΔΔQTcF are 90% CI from by-time point analysis while the error bars for concentration are 90% CI from descriptive statistics (0 was substituted as concentrations below 0 are not biologically plausible).
Figure 9:
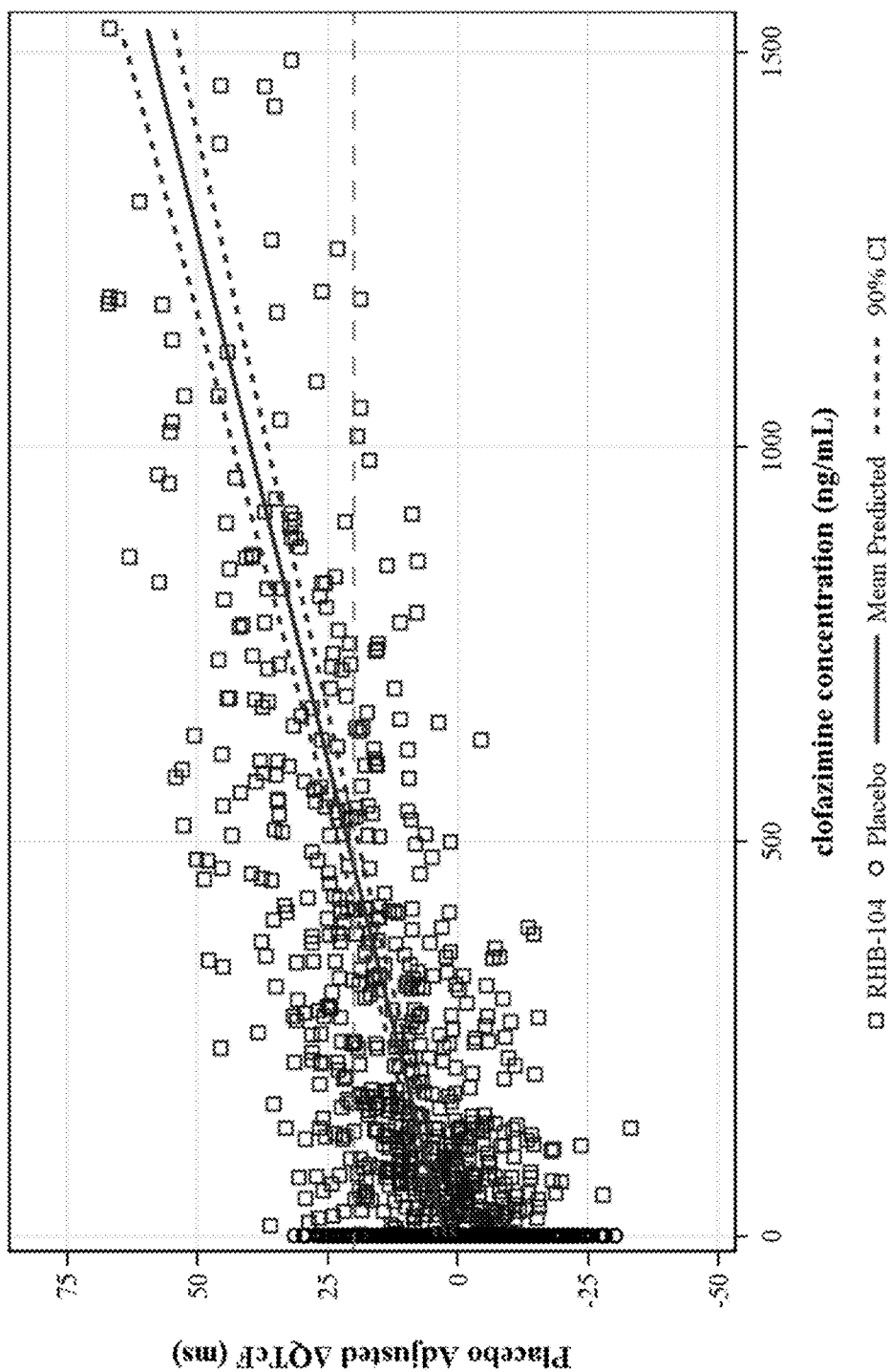
FIG. 9 is a scatter plot of observed plasma concentrations for clofazimine and estimated placebo-adjusted ΔQTcF (PK/QTc analysis set).

A joint plot of mean clofazimine concentration is shown in FIG. 8 and ΔQTcF suggested ΔQTcF increased as clofazimine concentration accumulated with repeated dosing over 52 weeks. The relationship between the individually observed clofazimine plasma concentrations and estimated placebo-adjusted ΔQTcF (i.e., ΔΔQTcF) is shown in FIG. 9. The solid line and the dotted line denotes the model-predicted mean ΔΔQTcF with 90% CI. The squares and circles denote the pairs of observed clofazimine plasma concentrations and estimated placebo-adjusted ΔQTcF by subjects for the RHB-104 and placebo treatment groups, respectively. The individually estimated placebo-adjusted $ΔQTcF_{i,j}$ equals the individual $ΔQTcF_{i,j}$ for subject i administered with RHB-104 at time point j minus the estimation of time effect at time point j.

The estimated population slope of the concentration-QTc relationship was 0.037 ms per ng/mL (90% CI: 0.0337 to 0.0410) with a treatment effect-specific intercept of 2.52 ms (90% CI: 0.76 to 4.29). Both the treatment effect-specific intercept and slope of clofazimine concentration were statistically significant at the 10% significance level (with P value of 0.0188 and <0.0001, respectively). A statistically significant treatment effect-specific intercept may indicate model misspecification. Given that the fit of the linear model is fully acceptable, nonlinear models were not considered, as it seems unlikely that such models would affect the predicted QTc at clinically relevant clofazimine plasma concentrations.

Example 7—Predicted QTcF Interval at Various Mean Clofazimine Concentrations

To enable the selection of a clofazimine dose which minimizes the QTc prolongation risk whilst preserving the clinical benefit in patients treated for NTM, model predictions were performed where the anticipated clofazimine $C_{max}$ obtained from PK model simulations was used as the input into the concentration-QT model previously described. In an ideal scenario, the selected dose(s) would be as close to those predicted to be associated with efficacy in the treatment with NTM yet associated with a QTc prolongation of <20 ms. This threshold of risk is deemed acceptable in patients with high morbidity associated with disease, requiring treatment with a QT prolonging drug.

As detailed in Example 4, the steady-state PK of each component was simulated using a Population Pharmacokinetic (popPK) model previously developed for analyzing the data from the MAP Study with RHB-104. The final popPK model was used to derive the Bayesian posthoc PK parameters for the patients enrolled in the MAP Study, as well as to simulate, in a virtual population, the concentration vs. time profile for each component (and metabolite where applicable) of the FDC product of the present disclosure. It was also used to simulate alternative dosing regimens to enable estimation of PK parameters of interest after 26 weeks and 52 weeks of treatment. Varying mg doses and frequency of clofazimine administration were simulated to characterize the relationship between dose and QTc prolongation liability.

Figure 10:
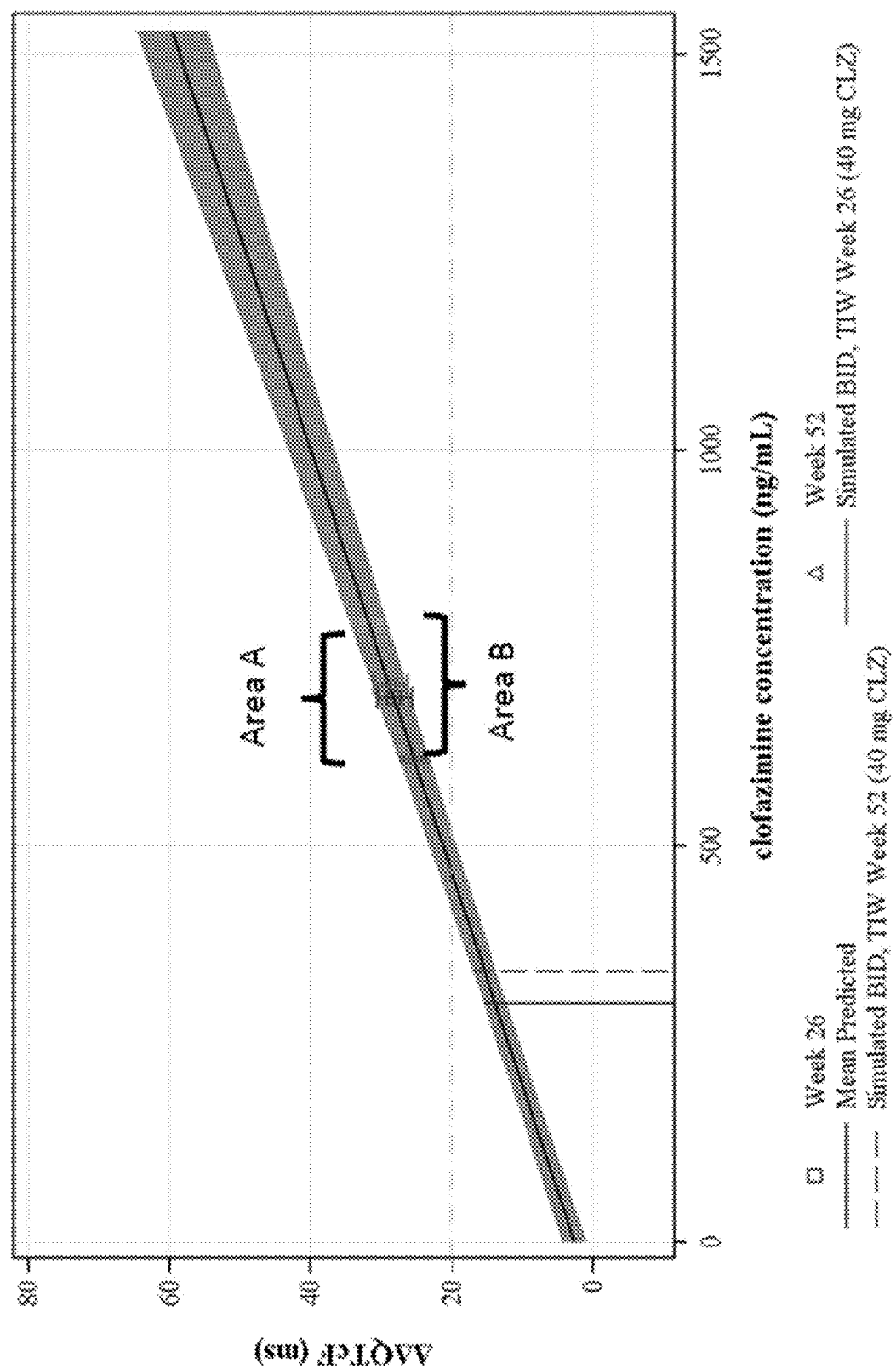
FIG. 10 is a plot showing predicted ΔΔQTcF at mean of clofazimine concentration. The solid line with gray shaded area denotes the model-predicted mean (90% CI) ΔΔQTcF. Area A and Area B denotes the estimated mean (90% CI) ΔΔQTcF with square and diamond at the mean (90% CI) of clofazimine for the RHB-104 at Week 26 and Week 52, respectively. The solid line denotes the simulated BID, TIW Week 26 (40 mg CLZ) at (301.37 ng/mL) while the dashed line denotes the simulated BID, TIW Week 52 (40 mg CLZ) at (341.87 ng/mL).

Secondary PK parameters were derived for each simulated regimen, including $C_{max}$ to enable predictions of the mean ΔΔQTcF in each simulated regimen. The linear mixed-effect model was then employed to predict the mean (90% confidence interval [CI]) ΔΔQTcF for each regimen. The predicted ΔΔQTcF at the mean (90% CI) clofazimine concentrations are presented in Table 23 and FIG. 10.

The predicted ΔΔQTcF at the observed clofazimine concentration at Week 52 is somewhat lower than the observed effect in the 'by time point' analysis, but results are relatively consistent when taking variability of plasma levels, the QTc effect and differences in analytical approach into account.

TABLE 23

Predicted ΔΔQTcF interval at mean clofazimine concentration

| Regimen | Mean (ng/mL) (90% CI) of clofazimine | ΔΔQTcF Estimate (ms) (90% CI) |
|---|---|---|
| Simulated BID, TIW Week 26 (20 mg CFZ) | 150.7 (36.74, 348.11) | 8.15 (6.53, 9.77) |
| Simulated BID, TIW Week 26 (25 mg CFZ) | 188.4 (45.93, 435.14) | 9.56 (7.95, 11.17) |
| Simulated BID, TIW Week 26 (30 mg CFZ) | 226.0 (55.11, 522.17) | 10.96 (9.35, 12.58) |
| Simulated BID, TIW Week 26 (40 mg CFZ) | 301.4 (73.48, 696.23) | 13.78 (12.12, 15.43) |
| Simulated BID, TIW Week 26 (50 mg CFZ) | 376.7 (91.85, 870.28) | 16.59 (14.85, 18.33) |
| Simulated∞ QD Week 52 (40 mg CFZ) | 365.5 (70.30, 958.80) | 16.17 (14.45, 17.89) |
| Simulated∞ QD Week 52 (50 mg CFZ) | 456.9 (87.88, 1198.50) | 19.58 (17.72, 21.45) |
| Simulated∞ BID, TIW Week 52 (20 mg CFZ) | 170.9 (36.80, 435.44) | 8.91 (7.29, 10.52) |
| Simulated∞ BID, TIW Week 52 (25 mg CFZ) | 213.7 (46.00, 544.31) | 10.50 (8.89, 12.11) |
| Simulated∞ BID, TIW Week 52 (30 mg CFZ) | 256.4 (55.20, 653.17) | 12.10 (10.47, 13.72) |
| Simulated∞ BID, TIW Week 52 (40 mg CFZ) | 341.9 (73.59, 870.89) | 15.29 (13.60, 16.98) |
| Simulated∞ BID, TIW Week 52 (50 mg CFZ) | 427.3 (91.99, 1088.61) | 18.48 (16.67, 20.29) |

Abbreviations: BID: Twice daily every day;
BID, TIW: Twice a day on Monday, Wednesday, Friday;
C-QT, concentration-QT;
QD: Once daily.
∞Represents mg dose per administration; for BID, TIW regimens, the Cmax was taken from the Friday PM dose
Cmax values were obtained by using the final population PK model developed for each drug component and predicted for each eligible subject in the PK population for Study RHB-104-01 as described in Certara report REDH-CSC-104.

Based on PK simulations, following 1 year of dosing (i.e. at Week 52) the anticipated mean (90% CI) $C_{max}$ following 40 mg BID-TIW of clofazimine (as part of a BID-TIW regimen) is predicted at 341.9 (73.59, 870.89) ng/mL, corresponding to a predicted mean (90% CI) ΔΔQTcF prolongation of 15.29 (13.60, 16.98) ms. This is below the 20 ms threshold of risk deemed acceptable in patients being treated for diseases associated with high morbidity.

While the coadministration of more than one drug with QTc prolongation potential would be expected to be at least additive, if not synergistic, the magnitude of the response and profile of ΔQTcF over time appears to mirror the pattern of clofazimine rise to steady-state over a period of three to six months of treatment. Selection of a 40 mg BID, M-W-F clofazimine dose, in combination with clarithromycin and rifabutin is predicted to result in a QTc prolongation of less than 20 ms, while predicted to also be efficacious based on nonclinical models of NTM lung infection caused by MAC.

Example 8—Phase 3 Study

For an investigational drug to receive approval from health authorities, it must undergo a rigorous non-clinical and clinical program to assess its safety and efficacy. FDA Phase 3 studies may or may not establish that a drug works to treat a particular disease or condition. Moreover, prior to completion and evaluation of Phase 3, a person of skill in the art would not necessarily understand that the drug is useful for treatment of the disease or condition or that the drug can be administered safely to any patient. A FDC product of the present invention is being tested in a Phase 3 study to demonstrate its efficacy in the treatment of patients with pulmonary NTM disease due to MAC with a dosing regimen of 3 capsules twice daily, three times weekly (M-W-F), see Table 24. These active ingredients and doses were selected to maximize therapeutic effectiveness against NTM, as well as minimizing potentially adverse events.

TABLE 24

Protocol for Phase 3 Study Testing a FDC for MAC lung disease

| | |
|---|---|
| Title | Study of Triple Antibiotic Fixed Dose Combination (FDC) Product for the Treatment of Pulmonary *Mycobacterium avium* Complex (MAC) Disease in Adults with Nodular Bronchiectasis (CleaR-MAC Trial) |
| Brief Summary | This is a 2-part multi-center, Phase 3, randomized, double-blind, placebo-controlled, parallel group study to evaluate the efficacy and safety of a triple antibiotic FDC in adult subjects with underlying nodular bronchiectasis and documented MAC lung infection. The primary efficacy endpoint at the end of Part 1 will be sputum culture conversion after 6 months of treatment. All subjects who have three consecutive monthly negative sputum cultures at Months 4, 5 and 6 will enter Part 2 and continue treatment with study drug to Month 16. Durability of response will be assessed at Month 19, 3 months post-completion of treatment.<br>Subjects who do not have three consecutive monthly negative sputum cultures at Months 4, 5 and 6 will discontinue study drug and enter Part 2 for follow-up until Month 19. |
| Phase | 3 |
| Study Type | Interventional |
| Objectives | Primary Objective<br>To assess the efficacy of a triple antibiotic FDC in the treatment of MAC lung disease as evidenced by sputum culture conversion (SCC) defined by three consecutive negative sputum cultures at Month 6.<br>Part 1 Secondary objectives<br>1. To assess the improvement in the Quality of Life Questionnaire - Bronchiectasis (QoL-B) Respiratory Symptoms domain at Month 6.<br>2. To assess the improvement in the Quality of Life Questionnaire - Bronchiectasis (QoL-B) Physical Functioning domain at Month 6<br>3. To assess the time to culture conversion (month of first of three consecutive negative cultures)<br>Part 2 Secondary objectives<br>1. To assess the sustainability of SCC at the end of treatment (Month 16)<br>2. To assess the durability of SCC at the end of study (Month 19)<br>3. To assess the improvement in the Quality of Life Questionnaire - Bronchiectasis (QoL-B) Respiratory Symptoms domain at the end of study (Month 19)<br>4. To assess the improvement in the Quality of Life Questionnaire - Bronchiectasis (QoL-B) Physical Functioning domain at the end of study (Month 19)<br>Safety Objective<br>To assess the safety and tolerability of the FDC<br>PK/PD Objectives<br>To estimate the steady-state exposure of individual FDC components and the relationship between steady-state exposure, SSC, sustainability of conversion, durability of culture conversion at 3 months after cessation of treatment and adverse event rates |
| Number of Sites | This study will be conducted in up to 50 sites in the USA |
| Number of Subjects | Approximately 125 will be randomized |
| Condition | Pulmonary NTM disease due to MAC |
| Inclusion Criteria | 1. Males and females aged ≥18 years to ≤85 years of age, inclusively<br>2. Have a MAC lung infection documented by at least 2 positive cultures for MAC 12 months prior to screening, with at least one of them obtained within 3 months prior to randomization (cultures need to be at least 1 month apart). Cultures may be obtained from sputum or bronchial washings. |

TABLE 24-continued

Protocol for Phase 3 Study Testing a FDC for MAC lung disease

|  |  |
|---|---|
|  | 3. Have MAC lung infection with evidence of underlying nodular infiltrates and/or bronchiectasis on a chest computed tomography (Chest CT) within 6 months of screening. A high-resolution computed tomography (HR-CT) scan is preferred, if available.<br>4. Have symptoms of MAC lung infection that include one of the following: respiratory symptoms such as chronic cough, excessive mucous production, fatigue, dyspnea, hemoptysis or systemic symptoms such as fever, night sweats or loss of appetite.<br>5. Be treatment naïve, or if previously treated for MAC, have not received treatment within the 6 months prior to screening<br>6. In the opinion of the Investigator the patient's disease severity level is considered reasonable and acceptable to enable participation in a placebo-controlled clinical trial for at least 8 months (Part 1)<br>7. Be able to expectorate or be willing to undergo an induction, to produce sputum of sufficient volume and quality per the Investigator's discretion for mycobacterial culture.<br>8. Subject's weight is above 41 Kilograms or 90 pounds.<br>9. Subject agrees to use the following effective contraceptive methods throughout the study and for at least 4 months after last study drug administration, unless subject or partner of subject is post-menopausal or otherwise incapable of becoming pregnant by reason of surgery or tubal ligation, or has had a vasectomy (note: estrogen containing products are prohibited medications):<br>   a. diaphragm, cervical cap, contraceptive sponge or condom with spermicidal foam/gel/cream/suppository<br>   b. intra-uterine device (IUD)/intra-uterine system (IUS)<br>   c. progestogen injection (Depo-Provera ®) or implantable progestine (Nexplanon ®)<br>10. Be able and willing to comply with study drug administration, study visits and study procedures.<br>11. Subject has read and understood the Informed Consent form and has provided written informed consent to participate as shown by a signature of subject on the consent form. |
| Exclusion Criteria | 1. Cavitary lung disease as observed on a chest CT scan (cavitary lesions exceeding 2 cm in diameter).<br>2. Currently taking or treated in the 6 months prior to screening with any of the following: bedaquiline, clofazimine or any component of American Thoracic Society(ATS)/Infectious Diseases Society of America (IDSA) multi-drug recommended therapy (macrolides, ethambutol, rifabutins/rifampins) for MAC or other multi-drug regime for NTM lung disease<br>3. Clarithromycin minimum inhibitory concentration (MIC) ≥32 μg/mL on MAC isolates in screening sputum<br>4. Known hypersensitivity or suspected history of hypersensitivity reactions to clarithromycin, rifabutin, or clofazimine or other drugs in each class<br>5. Forced expiratory volume in 1 second (FEV1) of <30% predicted<br>6. Subjects requiring chronic supplemental oxygen use (including intermittent or continuous use)<br>7. Planned lung resection surgery for MAC lung disease<br>8. Severe renal impairment with CLcr < 50 mL/min<br>9. AST or ALT > 3 × ULN or total bilirubin 2 × ULN (except where total bilirubin increase is due to Gilbert syndrome)<br>10. Serum potassium, calcium and magnesium outside of central laboratory ranges (based on normal ranges as follows: potassium 3.5-5.8 mmol/L; magnesium 1.8-2.4 mg/dL and calcium 8.6-10.5 mg/dL)<br>11. Subjects with Cystic Fibrosis, prior solid organ or hematologic transplant<br>12. Immunosuppressant therapy (with the exception of low-dose oral corticosteroids equivalent to <10 mg oral prednisone/day). Inhaled steroids are acceptable if regimen is stable prior to screening or use is Pro Re Nata (PRN)<br>13. Current usage of inhaled products containing amikacin, tobramycin or gentamicin<br>14. History of ventricular arrhythmias or family history of Long QT syndrome, including torsades de pointes<br>15. Corrected QT (QTc) interval on electrocardiogram (ECG) >460 ms for females or >450 ms for males, calculated using Fridericia's formula (QTcF)<br>16. Treatment with any medication that causes QT prolongation within seven days, or 5 half-lives, whichever is longest, prior to initiation of study drug, or intention to use them throughout the study, including but not limited to: amiodarone, amitriptyline, citalopram (dose greater than 20 mg/day), dihydroergotamine, disopyramide, dofetilide, dronedarone, ergotamine, ibutilde, ondansetron or other 5-HT3 receptor antagonists, pimozide, procainamide, quinidine, quinine, quinolone, ranolazine, risperidone, sotalol and tolteridine. Investigators are directed to the following up-to-date web site listing QT-prolonging drugs: https://www.crediblemeds.org/index.php/drugsearch |

TABLE 24-continued

Protocol for Phase 3 Study Testing a FDC for MAC lung disease

|  |  |
|---|---|
|  | 17. Treatment with sensitive and/or narrow-therapeutic-range CYP3A substrates e.g. alfentanil, alprazolam, atorvastatin, aprepitant, lovastatin, voriconazole |
|  | 18. Treatment with sensitive and/or narrow-therapeutic-range substrates for P-glycoprotein (e.g. digoxin, dabigatran) or OATP1B1/OATP1B3 (e.g. atorvastatin, rosuvastatin) |
|  | 19. Treatment with moderate-strong inducers and inhibitors of CYP3A (e.g. carbamazepine, St. John's wort (hypericum perforatum), itraconazole, ketoconazole |
|  | 20. Treatment with moderate-strong inhibitors of CYP2C9 (e.g., amiodarone) |
|  | 21. Pregnancy or breastfeeding that will continue during treatment |
|  | 22. Active pulmonary tuberculosis at screening |
|  | 23. Evidence of *Mycobacterium kanassi*, *Mycobacterium xenopi* or *Mycobacterium abscessus* Complex in the past 12 months or on screening culture |
|  | 24. Positive antibodies or known infection with HIV1, HIV2 |
|  | 25. Positive surface antigen for Hepatitis B, or antibody to Hepatitis C If there is a positive Hep C antibody and/or history of previously treated Hepatitis C, HCV Polymerase Chain Reaction (PCR) needs to be undetectable and the patient has to be off medications for at least 6 months prior to screening, and considered as cured by the discretion of the treating hepatologist or infectious disease specialist |
|  | 26. Current drug or alcohol abuse or history of drug or alcohol abuse in the past 5 years |
|  | 27. History of malignancy within the most recent 3 years or current malignancy except for basal cell or squamous cell carcinoma of the skin. The patient must be in remission. |
|  | 28. Evidence of any significant hematological, hepatic, renal, cardiac, immunologic, pulmonary, metabolic, neurological, psychiatric or other disease that in the discretion of the Principal Investigator (PI) may interfere with the subject's ability to participate in the clinical trial |
|  | 29. Unable to communicate well and to comply with the study requirements |
|  | 30. Involved in any other investigational drug or device protocol within 3 months prior to screening |
| Subject Participation Duration | Subjects will receive study drug for a total of 8 months in Part 1. Subjects who have SCC in Part 1 (determined at Month 8), will continue on study drug for a total of 16 months (Part 1 and Part 2) and be followed through to 19 months to assess durability of SCC. Subjects who do not have SCC in Part 1, will discontinue study drug at Month 8 and will be encouraged to remain in the study until the end of the study at Month 19 to complete study visits and procedures. Subjects who discontinue study drug and initiate rescue therapy (alternative anti-NTM treatment), at the Investigator's discretion, will also be encouraged to remain in the study until Month 19 for observation. |
| Sex/Gender | All |
| Ages | ≥18 years to ≤85 years, inclusive |
| Treatment | Investigational Drug: FDC Product: an all-in-one capsule containing a fixed combination of clarithromycin 158.3 mg, rifabutin 40 mg, and clofazimine 13.3 mg.<br>Matching Placebo |
| Route of Administration | Oral |
| Dose Regimen for Investigational Product | The target dose of study drug will be 3 FDC capsules administered BID each day on three days a week (Monday, Wednesday, Friday).<br>Each FDC capsule contains clarithromycin 158.3 mg; rifabutin 40 mg; clofazimine 13.3 mg.<br>The total daily dose will be titrated up over the first 2 weeks and will remain stable thereafter.<br><br>|  | Week 1 | Week 2 | Week 3 until end of treatment |<br>|---|---|---|---|<br>| FDC/Placebo | 3 capsules Once daily MWF | 3 capsules Once daily MWF | 3 capsules Twice daily MWF |<br><br>MWF = Monday, Wednesday, and Friday<br>The dose is 3 capsules (total of 474.9 mg clarithromycin; 120 mg rifabutin and 39.9 mg clofazimine) administered twice a day, resulting in a target daily dose of 949.8 mg clarithromycin, 240 mg rifabutin and 79.8 mg clofazimine, three times per week (on Mondays-Wednesdays-Fridays)<br>Study drug should be taken with food. |
| Study Design | Subjects meeting eligibility criteria will be randomized to receive FDC or matching placebo in a 3:2 ratio.<br>Randomization will be stratified by prior or no prior NTM lung disease treatment.<br>At the Month 8 visit, when all culture results from the first 6 months are available, culture results will be reviewed by the Investigator, and subjects will be categorized as either sputum culture converters or non-converters at Month 6, based on culture results at Months 4, 5, 6 (Part 1). Prior to Month 8 sputum culture results will not be available to the site or sponsor. |

TABLE 24-continued

Protocol for Phase 3 Study Testing a FDC for MAC lung disease

|  |  |
|---|---|
|  | Subjects with SCC in Part 1, defined by three consecutive negative sputum cultures at Months 4, 5 and 6 (treatment success) will enter Part 2 and continue treatment with study drug to Month 16.<br>Subjects who do not have SCC in Part 1 will be considered treatment failures. They will discontinue study drug and will continue into Part 2 of the study to undergo all study visits and procedures.<br>Durability of culture conversion for subjects with SCC at Month 6 (Part 1), will be assessed at Month 19, 3 months post-treatment completion.<br>Antimicrobial treatment for NTM for study treatment failures will be made available at the discretion of the Investigator. All subjects who discontinue study drug and continue with the study and receive rescue therapy, will be considered failures, regardless of any benefit received from rescue therapy.<br>Isolates will be banked for possible genotyping at the completion of the study. Genotyping will be done on samples from subjects who experienced at least two positive cultures after having SCC by Month 6. This will be done to determine whether relapse represents a new infection (different genotype) or recurrence of the baseline infection (same genotype).<br>In Part 2, sputum culture results will be available to the site and sponsor. Subjects whose positive cultures and isolates have sustained pan-sensitivity to FDC components, will remain on study drug and continue in the study. Subjects whose positive cultures and isolates have developed macrolide resistance (MIC ≥32 µg/mL) or an 8-fold increase in the rifabutin or clofazimine MICs compared to baseline, will discontinue study drug. These subjects will be encouraged to remain in the study for continued monitoring, including scheduled procedures and assessments.<br>Physician study visits will include screening to confirm eligibility, Baseline and visits at Months 1, 3, 4, 5, 6, 8, 11, 14, completion of treatment at Month 16, and 3 months post treatment at Month 19. At each clinic visit (including screening), review of concomitant medications, review of adverse events, and physical exam will be performed. ECGs will be done at clinic visits. An additional visit for ECG evaluation will be done at Week 2 between baseline and Month 1 visits. Chest CT scan will be performed at screening (if no CT scan is available within the 6 months prior to screening) and at the end of treatment (Month 16). Expectorated or induced sputum will be collected monthly until completion of treatment, and again at the 3-months post treatment visit to determine changes in mycobacterial smear and culture status. Home visits will be conducted (Months 2, 7, 9, 10, 12, 13 and 15) where a healthcare professional will collect expectorated sputum and record any adverse events and concomitant medications.<br>Quality of Life-Bronchiectasis (QoL-B) with NTM Module will be performed at screening, baseline, Months 4, 6, 11, 16 (completion of treatment) and Month 19 (3 months post treatment).<br>The PROMIS Fatigue 8a, SF-36 and Patient Global Impression of Severity (PGIS) questionnaires will be performed at baseline, Months 4, 6, 11, 16 (completion of treatment) and Month 19 (3 months post treatment).<br>The St. George's Respiratory Questionnaire (SGRQ) will be performed at baseline, Months 6 16 (completion of treatment) and Month 19 (3 months post treatment).<br>The Patient Global Impression of Change (PGIC) will be performed at Months 4, 6, 11, 16 (completion of treatment) and Month 19 (3 months post treatment). |
| Primary Endpoint | The proportion of subjects who achieve SCC by Month 6, defined by three consecutive monthly negative sputum cultures, without reversion, at Months 4, 5 and 6 for FDC compared to placebo |
| Part 1 Secondary Endpoints | 1. The mean change in Quality of Life Questionnaire-Bronchiectasis (QoL-B) Respiratory Symptoms domain scores domain scores from baseline to Month 6 for FDC compared to placebo<br>2. The mean change in Quality of Life Questionnaire-Bronchiectasis (QoL-B) Physical Functioning domain scores from baseline to Month 6 for FDC compared to placebo<br>3. The time to SCC (month of first negative sputum culture) for FDC compared to placebo |
| Part 2 Secondary Endpoints | 1. The proportion of subjects with SCC by Month 6 who sustain negative sputum cultures at Month 16 (end of treatment) and negative sputum culture at Month 19 (3 months off treatment) for FDC compared to placebo (durable responders)<br>2. The proportion of subjects with SCC by Month 6 who sustain negative sputum cultures at Month 16 (end of treatment) for FDC compared to placebo<br>3. The mean change in Quality of Life Questionnaire-Bronchiectasis (QoL-B) Respiratory Symptoms domain scores from baseline to Month 19 for FDC compared to placebo<br>4. The mean change in Quality of Life Questionnaire-Bronchiectasis (QoL-B) Physical Functioning domain scores from baseline to Month 19 FDC compared to placebo |

TABLE 24-continued

Protocol for Phase 3 Study Testing a FDC for MAC lung disease

| | |
|---|---|
| Pharmacokinetic/<br>Pharmacodynamic<br>Endpoints | 1. Estimate of the steady-state exposure of individual FDC components<br>2. Explore the relationship between steady-state FDC exposure, sputum culture conversion, sustainability and durability<br>3. Explore the relationship between steady-state FDC exposure and adverse event rates |
| Safety Endpoint | To evaluate the safety and tolerability of FDC in adult subjects with underlying nodular bronchiectasis and MAC lung infection |
| Study Completion | The primary efficacy analysis will be conducted after all subjects have completed the Month 8 visit at the end of Part 1. All analyses conducted in Part 1 will be final analyses for all endpoints evaluating data to Month 6. These final analyses include the primary endpoint and Part 1 secondary and exploratory endpoints evaluating Month 6 data. All safety data, available at the time of these analyses, will be summarized. To maintain the blinding of the study throughout Part 2, two teams will be formed: 1) a blinded team, which will continue to monitor the conduct of the study and 2) an unblinded team, which will evaluate the analyses and prepare the data for New Drug Application (NDA) submission. The Sponsor will make all efforts for these teams to remain separated by a firewall until the final database lock for the study.<br>The remaining analyses of sustained and durable culture conversion, comparisons from baseline to Months 16 and 19 and final safety analyses will be conducted after completion of Part 2 (last subject completes 3 months of post-treatment follow-up at Month 19). |

All, documents, patents, patent applications, publications, product descriptions, and protocols which are cited throughout this application are incorporated herein by reference in their entireties for all purposes.

Disclosed herein in an embodiment is a fixed-dose combination drug product comprising clarithromycin, clofazimine and rifabutin, wherein the fixed-dose combination drug product comprises a fixed dose of about 158.3 milligram (mg) of clarithromycin, a fixed dose of about 13.3 milligram (mg) of clofazimine and a fixed dose of about 40.0 milligram (mg) rifabutin. In an embodiment, the fixed-dose combination drug product is suitable for oral administration. In an embodiment, the fixed-dose combination drug product is a capsule. In an embodiment, the clofazimine of the fixed-dose combination drug product is dispersed in a carrier. In an embodiment, the clofazimine of the fixed-dose combination drug product is dispersed in polyethylene glycol. In an embodiment, the fixed-dose combination drug product is used in a method comprising orally administering the drug product to a patient in need of pulmonary Mycobacterium avium complex (MAC) disease therapy.

Disclosed herein in an embodiment is a fixed-dose combination drug product comprising clarithromycin, clofazimine and rifabutin, wherein the fixed-dose combination drug product comprises a fixed 158.3 milligram (mg) dose of clarithromycin, a fixed 13.3 milligram (mg) dose of clofazimine and a fixed 40.0 milligram (mg) dose of rifabutin. In an embodiment, the fixed-dose combination drug product is suitable for oral administration. In an embodiment, the fixed-dose combination drug product is a capsule. In an embodiment, the clofazimine of the fixed-dose combination drug product is dispersed in a carrier. In an embodiment, the clofazimine of the fixed-dose combination drug product is dispersed in polyethylene glycol. In an embodiment, the fixed-dose combination drug product is used in a method comprising orally administering the drug product to a patient in need of pulmonary Mycobacterium avium complex (MAC) disease therapy.

Disclosed herein in an embodiment is a three-drug combination of clarithromycin, clofazimine and rifabutin sufficiently designed for use in the treatment of pulmonary Mycobacterium avium complex (MAC) disease in a human subject. In an embodiment, the three-drug combination product has a fixed 158.3 milligram (mg) dose of clarithromycin, a fixed 13.3 milligram (mg) dose of clofazimine and a fixed 40.0 milligram (mg) dose of rifabutin. In an embodiment, the three-drug combination product is suitable for oral administration. In an embodiment, the three-drug combination product is a capsule. In an embodiment, the three-drug combination product is used in a method comprising orally administering the drug product to a patient in need of pulmonary Mycobacterium avium complex (MAC) disease therapy.

Disclosed herein in an embodiment is a method for treating pulmonary Mycobacterium avium complex (MAC) disease in an individual having a documented MAC lung infection, the method comprising administering to the individual once daily about 475 milligram (mg) of an oral dose of clarithromycin, about 40 milligram (mg) of an oral dose of clofazimine and about 120 milligram (mg) of an oral dose of rifabutin.

Disclosed herein in an embodiment is a method for treating pulmonary Mycobacterium avium complex (MAC) disease in an individual having a documented MAC lung infection, the method comprising administering to the individual twice daily about 475 milligram (mg) of an oral dose of clarithromycin, about 40 milligram (mg) of an oral dose of clofazimine and about 120 milligram (mg) of an oral dose of rifabutin.

Disclosed herein in an embodiment is a method for treating pulmonary Mycobacterium avium complex (MAC) disease in an individual having a documented MAC lung infection, the method comprising administering once daily at least one fixed-dose combination drug product comprising clarithromycin, clofazimine and rifabutin. In an embodiment, the fixed-dose combination drug product comprises a fixed 158.3 milligram (mg) dose of clarithromycin, a fixed 13.3 milligram (mg) dose of clofazimine and a fixed 40.0 milligram (mg) dose of rifabutin. In an embodiment, the method comprises administering once daily at least three fixed-dose combination drug products.

Disclosed herein in an embodiment is a method for treating pulmonary Mycobacterium avium complex (MAC) disease in an individual having a documented MAC lung infection, the method comprising administering twice daily at least one fixed-dose combination drug product comprising clarithromycin, clofazimine and rifabutin. In an embodiment, the fixed-dose combination drug product comprises a fixed 158.3 milligram (mg) dose of clarithromycin, a fixed 13.3 milligram (mg) dose of clofazimine and a fixed 40.0 milligram (mg) dose of rifabutin. In an embodiment, the method comprises administering twice daily at least three fixed-dose combination drug products.

Disclosed herein in an embodiment is a treatment regimen for treating pulmonary *Mycobacterium avium* complex disease in a patient, comprising orally administering to the patient at least three fixed-dose combination drug products, wherein each drug product comprises a fixed 158.3 milligram (mg) dose of clarithromycin, a fixed 13.3 milligram (mg) dose of clofazimine and a fixed 40 milligram (mg) dose of rifabutin, wherein the administering occurs on Monday-Wednesday-Friday for a period of time of at least six (6) months. In an embodiment, the patient takes about 475 milligram (mg) of clarithromycin, about 40 milligram (mg) of clofazimine and about 120 milligram (mg) of rifabutin on Monday-Wednesday-Friday for a period of time of at least six (6) months. In an embodiment, the regimen comprises orally administering to the patient at least six fixed-dose combination drug products. In an embodiment, the patient takes about 950 milligram (mg) of clarithromycin, about 80 milligram (mg) of clofazimine and about 240 milligram (mg) of rifabutin on Monday-Wednesday-Friday for a period of time of at least six (6) months. In an embodiment, the six fixed-dose combination drug products are administered to the patient in split doses.

Disclosed herein in an embodiment is a kit for treating pulmonary *Mycobacterium avium* complex (MAC) disease in an individual having a documented MAC lung infection comprising: a supply of fixed-dose combination drug products, wherein each of the fixed-dose combination drug products comprise a fixed 158.3 milligram (mg) dose of clarithromycin, a fixed 13.3 milligram (mg) dose of clofazimine and a fixed 40.0 milligram (mg) dose of rifabutin; and instructions for use. In an embodiment, the fixed-dose combination drug products are supplied as capsules. In an embodiment, the instructions for use state to orally administer three of the fixed-dose combination drug products from the supply two times daily on three days in a given week. In an embodiment, the instructions for use state to orally administer three of the fixed-dose combination drug products from the supply in the morning and three of the fixed-dose combination drug products from the supply in the evening on Monday-Wednesday-Friday of a week.

In an embodiment, a method for treating a human suffering from pulmonary nontuberculous mycobacterial disease due to *Mycobacterium Avium* Complex (MAC) comprises the steps of instructing the human to take three times per week a daily dose of 950 mg clarithromycin, 240 mg rifabutin, and 80 mg clofazimine, wherein a risk of QTc prolongation to the human is lower after 26 weeks following three times per week daily dosages of 950 mg clarithromycin, 240 mg rifabutin, and 80 mg clofazimine than it would be if the human took every day of the week 950 mg clarithromycin, 450 mg rifabutin and 100 mg clofazimine for 26 weeks.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed is:

1. A fixed-dose combination drug product formulated for oral delivery, the drug product comprising a fixed 158.3 milligram (mg) dose of clarithromycin, a fixed 13.3 milligram (mg) dose of clofazimine and a fixed 40.0 milligram (mg) dose of rifabutin.

2. The drug product of claim 1, wherein the clofazimine is dispersed in a hydrophilic or hydrophobic carrier.

3. The drug product of claim 2, wherein the carrier is polyethylene glycol.

4. The drug product of claim 1, further comprising one or more pharmaceutical excipients.

5. The drug product of claim 1 which is a capsule.

6. The drug product of claim 1 for use in treating pulmonary *Mycobacterium avium* Complex (MAC) disease in a subject in need thereof.

7. A method for treating pulmonary *Mycobacterium avium* Complex (MAC) disease in a human having MAC lung infection, the method comprising orally administering, once daily, about 475 milligram (mg) of clarithromycin, about 40 milligram (mg) of clofazimine and about 120 milligram (mg) of rifabutin.

8. The method of claim 7, wherein the about 475 milligram (mg) of clarithromycin, about 40 milligram (mg) of clofazimine and about 120 milligram (mg) of rifabutin is provided as 3 fixed-dose combination drug products, each drug product comprising a fixed 158.3 milligram (mg) dose of clarithromycin, a fixed 13.3 milligram (mg) dose of clofazimine and a fixed 40.0 milligram (mg) dose of rifabutin.

9. A method for treating pulmonary *Mycobacterium avium* Complex (MAC) disease in a human having MAC lung infection, the method comprising orally administering, twice daily, about 475 milligram (mg) of clarithromycin, about 40 milligram (mg) of clofazimine and about 120 milligram (mg) of rifabutin.

10. The method of claim 9, wherein the about 475 milligram (mg) of clarithromycin, about 40 milligram (mg) of clofazimine and about 120 milligram (mg) of rifabutin is provided as 3 fixed-dose combination drug products, each drug product comprising a fixed 158.3 milligram (mg) dose of clarithromycin, a fixed 13.3 milligram (mg) dose of clofazimine and a fixed 40.0 milligram (mg) dose of rifabutin.

11. A method for treating pulmonary *Mycobacterium avium* Complex (MAC) disease in a patient having MAC lung infection, the method comprising orally administering to the patient at least three fixed-dose combination drug products, wherein each drug product comprises a fixed 158.3 milligram (mg) dose of clarithromycin, a fixed 13.3 milligram (mg) dose of clofazimine and a fixed 40 milligram (mg) dose of rifabutin, and wherein the administering occurs only on Monday-Wednesday-Friday for a period of time of at least six (6) months.

12. The method of claim 11, wherein the administering occurs once daily on Monday-Wednesday-Friday for a period of time of at least six (6) months, and wherein the total daily dose comprises about 475 milligram (mg) of clarithromycin, about 40 milligram (mg) of clofazimine and about 120 milligram (mg) of rifabutin.

13. The method of claim 11, wherein the administering occurs twice daily on Monday-Wednesday-Friday for a period of time of at least six (6) months, and wherein the patient takes a total daily dose of about 950 milligram (mg) of clarithromycin, about 80 milligram (mg) of clofazimine and about 240 milligram (mg) of rifabutin.

14. The method of claim 13, wherein the total daily dose of about 950 milligram (mg) of clarithromycin, about 80 milligram (mg) of clofazimine and about 240 milligram (mg) of rifabutin is administered as six fixed-dose combination drug products.

15. The method of claim 14, wherein the six fixed-dose combination drug products are administered to the patient in split doses.

16. The method of claim 15, wherein the split doses includes three fixed-dose combination drug products, wherein the split doses are administered at one point of time during a day and three fixed-dose combination drug products are administered at a later point of time on the same day.

17. A kit for treating pulmonary *Mycobacterium avium* Complex (MAC) disease in an individual having MAC lung infection comprising: a supply of fixed-dose combination drug products, wherein each of the fixed-dose combination drug products comprise a fixed 158.3 milligram (mg) dose of clarithromycin, a fixed 13.3 milligram (mg) dose of clofazimine and a fixed 40.0 milligram (mg) dose of rifabutin; and instructions for use.

18. The kit of claim 17, wherein the fixed-dose combination drug products are supplied as capsules.

19. The kit of claim 17, wherein the instructions for use state to orally administer three of the fixed-dose combination drug products from the supply two times daily on three days each week.

20. The kit of claim 17, wherein the instructions for use state to orally administer three of the fixed-dose combination drug products from the supply in the morning and three of the fixed-dose combination drug products from the supply in the evening on Monday-Wednesday-Friday of a week.

* * * * *